(12) United States Patent
Hamada

(10) Patent No.: US 12,691,249 B2
(45) Date of Patent: Jul. 28, 2026

(54) SYSTEM

(71) Applicant: Softbank Group Corp., Tokyo (JP)

(72) Inventor: Masaki Hamada, Tokyo (JP)

(73) Assignee: SoftBank Group Corp., Tokyo (JP)

( * ) Notice: Subject to any disclaimer, the term of this patent is extended or adjusted under 35 U.S.C. 154(b) by 0 days.

(21) Appl. No.: 19/317,041

(22) Filed: Sep. 2, 2025

(65) Prior Publication Data

US 2026/0061156 A1    Mar. 5, 2026

(30) Foreign Application Priority Data

Sep. 4, 2024    (JP) ................................. 2024-152631

(51) Int. Cl.
| | |
|---|---|
| *A61M 21/02* | (2006.01) |
| *A61M 21/00* | (2006.01) |
| *A61N 1/04* | (2006.01) |
| *A61N 1/08* | (2006.01) |
| *G16H 20/30* | (2018.01) |

(52) U.S. Cl.
CPC ........... *A61M 21/02* (2013.01); *A61N 1/0484* (2013.01); *A61N 1/08* (2013.01); *G16H 20/30* (2018.01); *A61M 2021/0072* (2013.01)

(58) Field of Classification Search
None
See application file for complete search history.

(56) References Cited

U.S. PATENT DOCUMENTS

| | | | | |
|---|---|---|---|---|
| 2010/0114187 A1* | 5/2010 | Chan | ...................... | A61M 21/00 |
| | | | | 607/2 |
| 2014/0236272 A1* | 8/2014 | Simon | ...................... | A61P 25/06 |
| | | | | 607/145 |
| 2015/0297109 A1* | 10/2015 | Garten | ...................... | A61B 5/38 |
| | | | | 600/28 |

FOREIGN PATENT DOCUMENTS

JP    2022-180282 A    12/2022

* cited by examiner

*Primary Examiner* — Carrie R Dorna
(74) *Attorney, Agent, or Firm* — Banner & Witcoff, Ltd.

(57) ABSTRACT

The system includes a processor that works with a full-body fitting garment equipped with internal sensors and low-frequency pads. It collects biometric data, connects wirelessly to an external device via a control unit, and uses an AI module to visualize the user's relaxation state. Based on this, it generates instructions to optimize relaxation and controls the pads accordingly.

6 Claims, 14 Drawing Sheets

SYSTEM

CROSS-REFERENCE TO RELATED APPLICATION

This application claims priority under 35 USC 119 from Japanese Patent Application No. 2024-152631 filed Sep. 4, 2024, the disclosure of which is incorporated by reference herein in its entirety.

BACKGROUND

Technical Field

The present disclosure relates to a system.

Related Art

Japanese Patent Application Laid-Open (JP-A) No. 2022-180282 discloses a persona chatbot control method executed by at least one processor. The method includes steps of: receiving a user utterance, adding the user utterance to a prompt including a description of a chatbot character and an associated instruction sentence, encoding the prompt, and inputting the encoded prompt to a language model to generate a chatbot utterance responding to the user utterance.

Conventional massage devices and systems lack the ability to automatically and optimally adjust the massage program to suit an individual user's real-time physiological and psychological state. Users often experience suboptimal relaxation and effectiveness, as these systems do not continuously monitor biometric data or intelligently adapt the massage pattern. Furthermore, conventional solutions rarely provide a mechanism for learning from user feedback to improve future sessions, resulting in an inability to offer personalized and evolving massage experiences.

SUMMARY

The present invention provides a system comprising a full-body fitting garment equipped with sensors and low-frequency pads, a control unit connected to the garment, and an external information processing device wirelessly connected to the control unit. The system employs an artificial intelligence module that visualizes the user's relaxation state based on real-time biometric data collected by the sensors and generates operation instructions for optimizing the massage process. The control unit executes these instructions to control the low-frequency pads. Furthermore, the artificial intelligence module learns from user feedback, enabling the system to iteratively improve and personalize subsequent massage programs for each user.

"Full-body fitting garment" means a piece of clothing designed to closely adhere to the surface of the user's body and cover most or all areas, allowing for the placement and operation of embedded sensors and pads. "Sensor" means a device embedded within the garment, capable of detecting and measuring biometric data such as body temperature, heart rate, or skin conductance from the user.

"Low-frequency pad" means an electrode or similar element installed in the garment, capable of applying low-frequency electrical stimulation to the user's body for massage purposes.

"Control unit" means a device connected to the garment which manages the operation of the sensors and low-frequency pads, and which communicates with an external information processing device.

"External information processing device" means a separate computing device, such as a smartphone or tablet, which wirelessly connects to the control unit and processes data from the garment.

"Artificial intelligence module" means a software component installed in the external information processing device, configured to analyze biometric data, visualize user states, generate operation instructions, and learn from user feedback in order to optimize the massage program.

"Biometric data" means physiological parameters obtained from the user, including but not limited to body temperature, heart rate, and skin conductance, which are used to assess the user's physical or psychological state.

"Operation instructions" means signals or data generated by the artificial intelligence module, based on the analysis of biometric data, for controlling the activation, intensity, and rhythm of the low-frequency pads.

"User feedback" means subjective input or responses provided by the user after a massage session, describing the effectiveness or preferences for the massage, which are used to further personalize future massage programs.

BRIEF DESCRIPTION OF THE DRAWINGS

Exemplary embodiments of the present disclosure will be described in detail based on the following figures, wherein.

DETAILED DESCRIPTION

Figure 1:
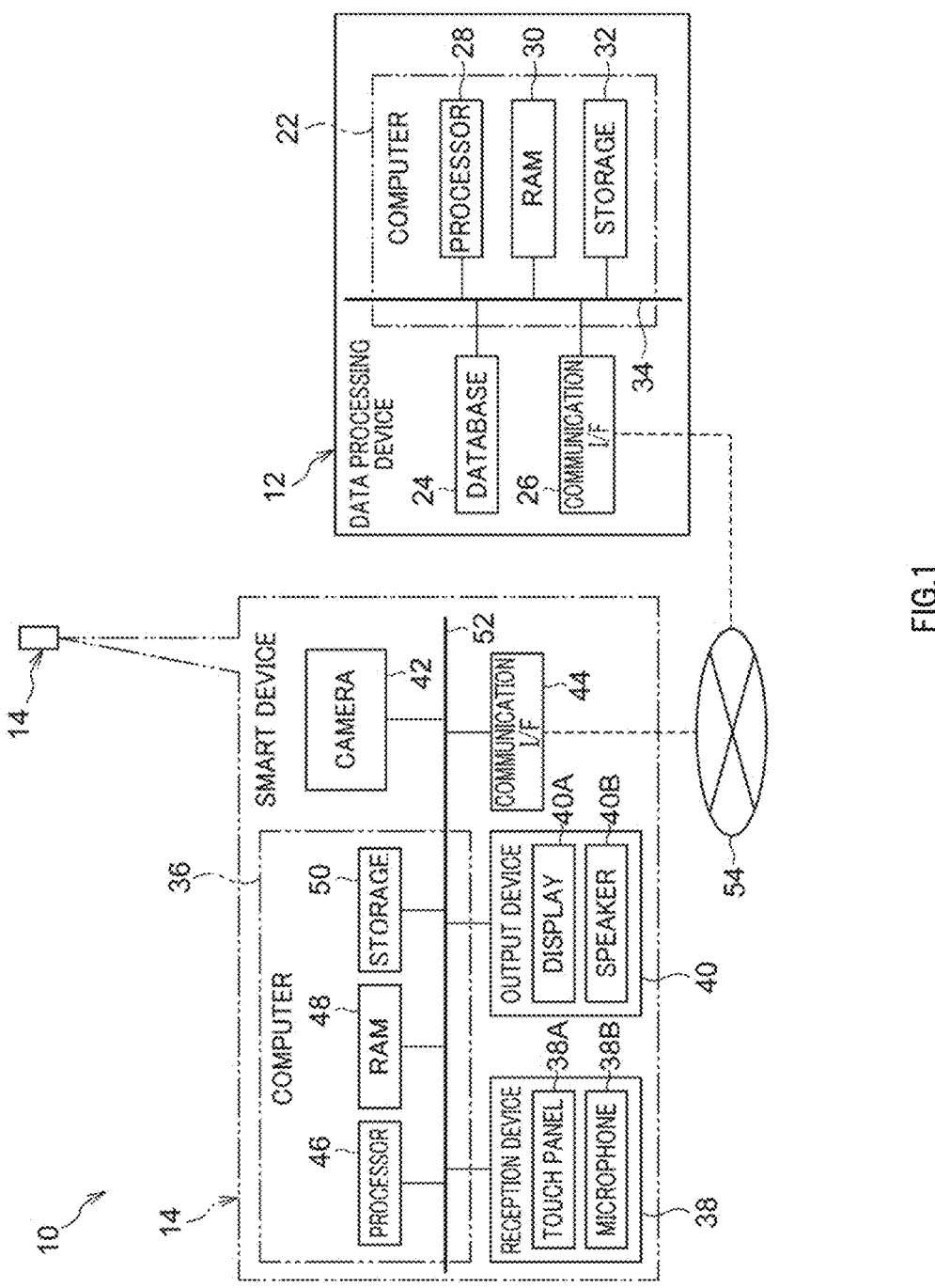
FIG. 1 is a schematic diagram illustrating an example of a configuration of a data processing system according to a first exemplary embodiment.

Description follows regarding an example of exemplary embodiments of a system according to technology disclosed herein, with reference to the appended drawings.

First, explanation follows regarding terminology employed in the following description.

In the following exemplary embodiments, a reference-numeral-appended processor (hereinafter simply referred to as "processor") may be implemented by a single computation unit, and may be implemented by a combination of plural computation units. The processor may be implemented by a single type of computation unit, or may be implemented by a combination of plural types of computation units. Examples of computation unit include a central processing unit (CPU), a graphics processing unit (GPU), a general-purpose computing on graphics processing units (GPGPU), an accelerated processing unit (APU), and the like.

In the following exemplary embodiments, random access memory (RAM) appended with a reference numeral is memory temporarily stored with information, and is employed as working memory by a processor.

In the following exemplary embodiments, reference-numeral-appended storage is a single or plural non-volatile storage devices for storing various programs and various parameters and the like. Examples of non-volatile storage devices include flash memory (such as a solid state drive (SSD)), a magnetic disk (for example, a hard disk), magnetic tape, and the like.

In the following exemplary embodiments, a reference-numeral-appended communication interface (I/F) is an interface including a communication processor and an antenna or the like. The communication I/F has the role of communicating between plural computers. An example of a communication standard applied for the communication I/F is a wireless communication standard, such as a Fifth Generation Mobile Communication System (5G), Wi-Fi (registered trademark), Bluetooth (registered trademark), and the like.

In the following exemplary embodiments "A and/or B" has the same definition as "at least one out of A or B". Namely, "A and/or B" may mean A alone, may mean B alone, or may mean a combination of A and B. Moreover, similar logic to "A and/or B" is applied when "and/or" is employed to link three or more items in the present specification.

First Exemplary Embodiment

FIG. 1 illustrates an example of a configuration of a data processing system 10 according to a first exemplary embodiment.

As illustrated in FIG. 1, the data processing system 10 includes a data processing device 12 and a smart device 14. A server is an example of the data processing device 12.

The data processing device 12 includes a computer 22, a database 24, and a communication I/F 26. The computer 22 is an example of a "computer" according to technology disclosed herein. The computer 22 includes a processor 28, RAM 30, and storage 32. The processor 28, the RAM 30, and the storage 32 are connected to a bus 34. The database 24 and the communication I/F 26 are also connected to the bus 34. The communication I/F 26 is connected to a network 54. Examples of the network 54 include a Wide Area Network (WAN) and/or a local area network (LAN).

The smart device 14 includes a computer 36, a reception device 38, an output device 40, a camera 42, and a communication I/F 44. The computer 36 includes a processor 46, RAM 48, and storage 50. The processor 46, the RAM 48, and the storage 50 are connected to a bus 52. The reception device 38, the output device 40, the camera 42, and the communication I/F 44 are also connected to the bus 52.

The reception device 38 includes a touch panel 38A, a microphone 38B, and the like for receiving user input. The touch panel 38A receives user input from contact of a pointer (for example, a pen, a finger, or the like) by detecting contact of the pointer. The microphone 38B receives spoken user input by detecting speech of the user. A control unit 46A in the processor 46 transmits data representing the user input received by the touch panel 38A and the microphone 38B to the data processing device 12. A specific processing unit 290 in the data processing device 12 acquires the data indicating the user input.

The output device 40 includes a display 40A, a speaker 40B, and the like for presenting data to a user 20 by outputting the data in an expression format perceivable by the user 20 (for example, audio and/or text). The display 40A displays visual information such as text, images, or the like under instruction from the processor 46. The speaker 40B outputs audio under instruction from the processor 46. The camera 42 is a compact digital camera installed with an optical system such as a lens, an aperture, a shutter, and the like, and with an imaging device such as a complementary metal-oxide semiconductor (CMOS) image sensor or a charge coupled device (CCD) image sensor or the like.

The communication I/F 44 is connected to the network 54. The communication I/F 44 and the communication I/F 26 perform the role of exchanging various information between the processor 46 and the processor 28 over the network 54.

Figure 2:
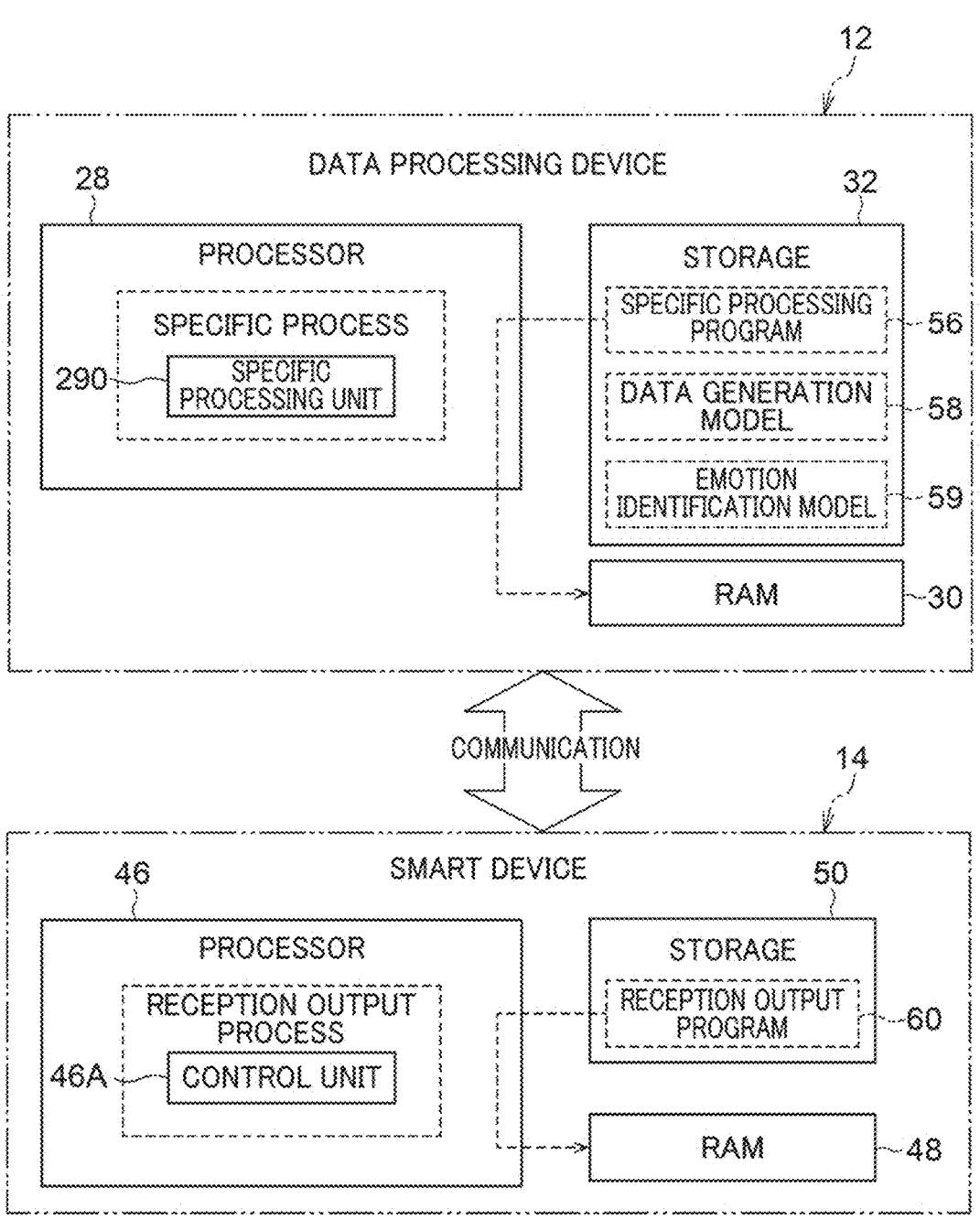
FIG. 2 is a schematic diagram illustrating an example of relevant functions of a data processing device and a smart device according to the first exemplary embodiment.

FIG. 2 illustrates an example of relevant functions of the data processing device 12 and the smart device 14.

As illustrated in FIG. 2, specific processing is performed by the processor 28 in the data processing device 12. A specific processing program 56 is stored in the storage 32. The specific processing program 56 is an example of a "program" according to technology disclosed herein. The processor 28 reads the specific processing program 56 from the storage 32, and in the RAM 30 executes the read specific processing program 56. The specific processing is implemented by the processor 28 operating as the specific processing unit 290 according to the specific processing program 56 executed in the RAM 30.

A data generation model 58 and an emotion identification model 59 are stored in the storage 32. The data generation model 58 and the emotion identification model 59 are employed by the specific processing unit 290. The specific processing unit 290 uses the emotion identification model 59 to estimate an emotion of a user, and is able to perform the specific processing using the user emotion. In an emotion estimation function (emotion identification function) that uses the emotion identification model 59, various estimations, predictions, and the like are performed related to emotions of the user, include estimating and predicting the emotion of the user, however, there is no limitation to such examples. Moreover, estimation and prediction of emotion also includes, for example, analyzing (parsing) emotions and the like.

Reception and output processing is performed by the processor 46 in the smart device 14. A reception and output program 60 is stored in the storage 50. The reception and output program 60 is employed by the data processing system 10 in combination with the specific processing program 56. The processor 46 reads the reception and output program 60 from the storage 50, and in the RAM 48 executes the read reception and output program 60. The reception and output processing is implemented by the processor 46 operating as the control unit 46A according to the reception and output program 60 executed in the RAM 48. Note that a configuration may be adopted in which a similar data generation model and emotion identification model to the data generation model 58 and the emotion identification model 59 are included in the smart device 14, and these models are used to perform similar processing to the specific processing unit 290. The reception and output program is implemented by the processor 46 operating as the control unit 46A according to the reception and output program 60 executed in the RAM 48.

Note that devices other than the data processing device 12 may include the data generation model 58. For example, a server device (for example, a generation server) may include the data generation model 58. In such cases, the data processing device 12 performs communication with the server device including the data generation model 58 to obtain a processing result (prediction result or the like) obtained using the data generation model 58. The data processing device 12 may be a server device, and may be a terminal device owned by the user (for example, a mobile phone, a robot, a home electrical appliance, or the like). Next, description follows regarding an example of processing by the data processing system 10 according to the first exemplary embodiment.

Example 1

Description follows regarding a flow of the specific processing in an Example 1. The units of the system described below are implemented by the data processing device 12 and the smart device 14. The data processing device 12 is called a "server" and the smart device 14 is called a "terminal".

Conventional massage systems have difficulty providing an optimal massage program tailored to each user's current physiological and relaxation state. Fixed programs fail to adequately consider individual biosignals or real-time feedback, resulting in insufficient relaxation effects and suboptimal user satisfaction. Additionally, it is challenging to dynamically adapt massage patterns based on ongoing user feedback and physiological changes, thereby limiting continuous personalization and improvement of the relaxation experience.

The specific processing by the specific processing unit 290 of the data processing device 12 in Example 1 is realized by the following means.

The present invention provides a server comprising a processor configured to acquire biosignal data from a wearable garment, transmit the biosignal data to an information processing device equipped with a generative artificial intelligence model, analyze and calculate a user state index based on the acquired data, generate individualized stimulation signal patterns by means of prompt sentences and usage context, and control a stimulation signal generation device in accordance with the generated patterns as well as continuously improve the personalization of future programs by learning from user feedback. This enables highly adaptive, real-time, and user-specific massage experiences that maximize relaxation and address the shortcomings of conventional fixed-pattern massage systems.

The term "biosignal data" refers to physiological signals acquired from a user, including but not limited to heart rate, body temperature, and skin conductance, which reflect the user's physical and emotional state.

The term "wearable garment" refers to a clothing article designed to maintain close contact with a user's body, equipped with integrated electronics such as biosignal detection devices and stimulation signal generation devices.

The term "biosignal detection device" refers to an electronic component embedded within the wearable garment that is capable of sensing, measuring, and converting user biosignals into digital data for analysis.

The term "stimulation signal generation device" refers to an electronic component incorporated into the wearable garment that delivers stimulation, such as electrical signals, to specific areas of the user's body in accordance with control instructions.

The term "control device" refers to a hardware component connected to the wearable garment, configured to interface with and control the biosignal detection device and the stimulation signal generation device, and to manage communication with external information processing devices.

The term "information processing device" refers to an external computing apparatus, such as a smartphone or tablet, configured to receive biosignal data, analyze physiological data, and generate control instructions based on computational models.

The term "generative artificial intelligence model" refers to a computational system utilizing machine learning algorithms, such as neural networks, to analyze input data, extract patterns, calculate user state indices, and generate individualized stimulation signal patterns.

The term "user state index" refers to a quantitative value derived from biosignal data analysis, representing a user's current relaxation, stress, or other physiological status.

The term "stimulation signal pattern" refers to a set of instructions determining the timing, location, intensity, and frequency of stimulation delivered by the stimulation signal generation device to the user's body.

The term "prompt sentence" refers to a structured textual input used to guide the generative artificial intelligence model in generating individualized stimulation signal patterns based on user context and biosignal data.

The term "integrated power storage element" refers to an energy storage component, such as a rechargeable battery, housed within the control device to supply operational power.

One embodiment of the invention provides a system for optimizing user relaxation by analyzing biosignal data from a user and controlling a stimulation signal generation device incorporated into a wearable garment, using a generative artificial intelligence model and prompt sentences. The system includes a wearable garment, a control device, an information processing device, and a processor configured to execute the program for the entire process.

The wearable garment is designed to maintain close contact with the user's body and incorporates at least one biosignal detection device, such as a heart rate sensor, temperature sensor, and skin conductance sensor, as well as at least one stimulation signal generation device, such as a low-frequency electrode pad. The hardware components can be, for example, flexible circuits and electrodes embedded into fabric, digital thermistors, optical heart rate sensors, and galvanic skin response modules. The stimulation signal generation device typically consists of an electrical stimulator capable of delivering variable frequency and intensity signals to the body.

The control device, which may be embodied as a microcontroller with integrated wireless communication functionality (such as an ARM Cortex-M microcontroller with Bluetooth or Wi-Fi module), is physically coupled to the wearable garment. The control device is powered by an integrated rechargeable battery. It manages acquisition of biosignal measurements from the biosignal detection devices and actuates the stimulation signal generation device upon receiving external instructions.

The information processing device, typically realized by a general-purpose computing device such as a smartphone or tablet, establishes wireless communication with the control device. The information processing device is programmed to receive biosignal data from the wearable garment through the control device, pre-process the data for validity, and transmit it via a secure communication protocol (for example, HTTPS) to a remote server for advanced analysis, or to perform such analysis locally depending on the deployment.

A server, implemented using general server hardware (for instance, a Linux-based cloud virtual machine), is installed with the generative artificial intelligence model, which leverages machine learning frameworks such as PyTorch or TensorFlow. The server receives biosignal data and, using a prompt sentence describing the user's context and needs, analyzes the data to calculate a user state index, such as a relaxation score. The generative artificial intelligence model then generates an individualized stimulation signal pattern optimized to maximize the relaxation score.

For example, a prompt sentence provided to the generative artificial intelligence model could be:

"Please generate an optimal massage program for a user whose heart rate is 78 bpm, body temperature is 36.6° C., and skin conductance is 8 μS. The user is experiencing shoulder and back discomfort after prolonged desk work. Propose low-frequency stimulation parameters to maximize relaxation index."

The server then transmits the result—a set of control parameters describing the area, frequency, duration, and timing of stimulation—to the information processing device, which, in turn, sends the command wirelessly to the control device. The control device activates the stimulation signal generation device to provide the personalized massage pattern in real time. The user experiences this automatic, adaptive massage pattern. After completion of the session, the system prompts the user to supply feedback about the effectiveness or comfort of the stimulation via the information processing device. This feedback is sent to the server and used as supervised training data to update the generative artificial intelligence model, thereby allowing the system to continually improve personalization with repeated use.

As a concrete example, when a user wears the garment during or after extended desk work, the system continuously monitors physiological indicators, calculates a real-time relaxation index, adapts the control of the low-frequency stimulators accordingly, and prompts the user for session-specific feedback, assuring evolving optimization unique to each individual.

Thus, this embodiment illustrates the practical construction and use of the system by specifying hardware, software, and the interplay between sensing, machine learning, control, and user feedback mechanisms—enabling highly tailored stimulation for effective user relaxation.

Figure 11:
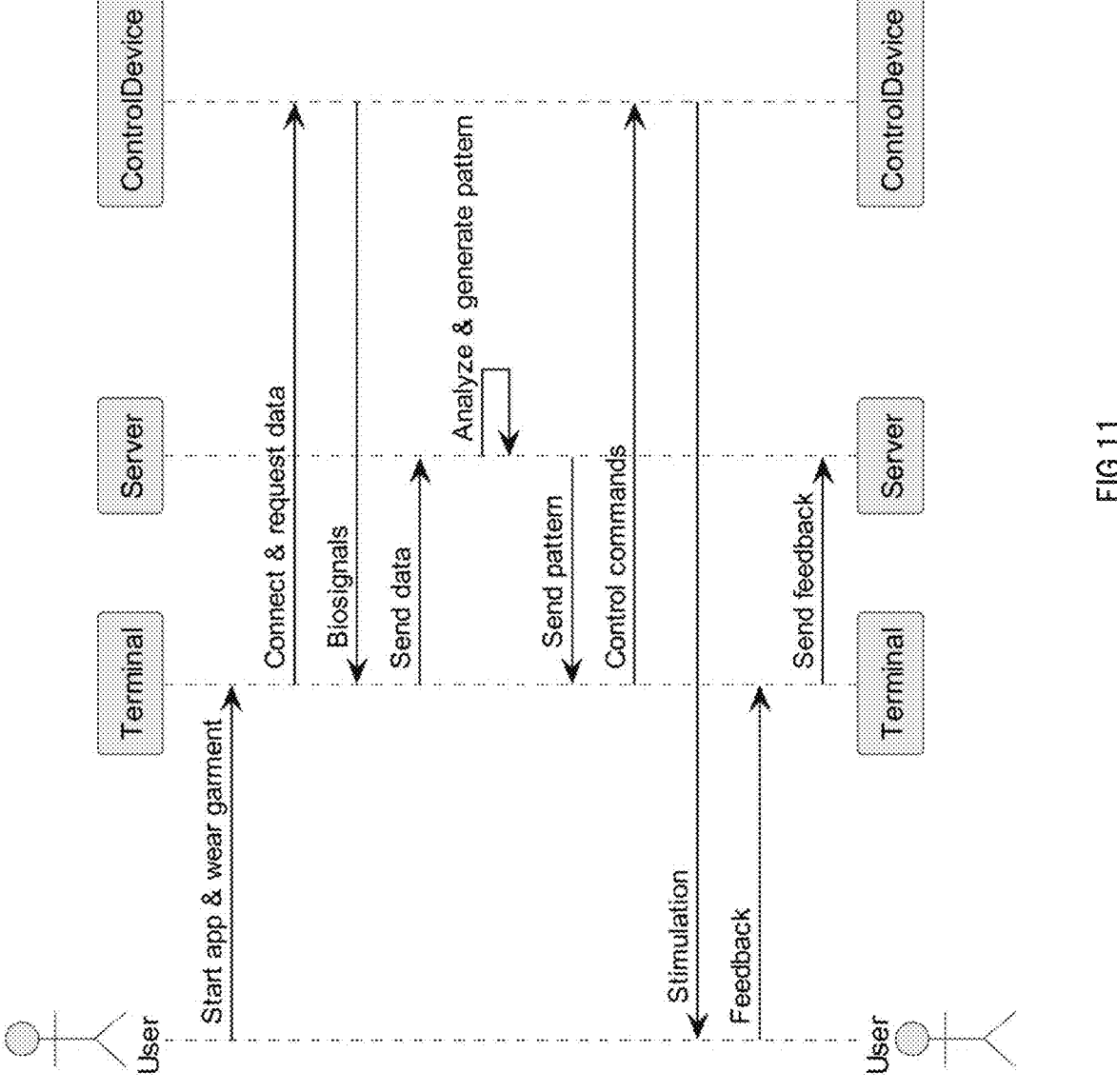
FIG. 11 is a sequence diagram showing the flow of data processing system processing in Example 1.

The following describes the processing flow using FIG. 11.

Step 1

User wears the wearable garment, ensuring that all embedded biosignal detection devices (heart rate, temperature, and skin conductance sensors) are in proper contact with the skin. The user then launches the dedicated application on the information processing device (smartphone or tablet) and powers on the control device.

Input: User's physical interaction and initial device status.

Data processing: No digital processing, but hardware initialization and device checks are performed.

Output: System is ready with all sensors activated and connected.

Step 2

Terminal (information processing device) establishes a wireless (Bluetooth or Wi-Fi) connection with the control device. The terminal issues a command to the control device to begin biosignal acquisition.

Input: Wireless device discovery and pairing request.

Data processing: Authentication and device handshake using standard wireless communication protocols.

Output: Secure communication established between terminal and control device.

Step 3

Control device collects real-time biosignal data from the sensors embedded in the garment and converts analog signals into digital format. The terminal periodically receives these digitized data packets.

Input: Analog sensor outputs (heart rate, temperature, skin conductance).

Data processing: Analog-to-digital conversion, data structuring, and error checking.

Output: Digital biosignal data streams transferred to terminal.

Step 4

Terminal validates and formats the received biosignal data, temporarily storing it and preparing it for further processing.

Input: Raw digital biosignal data.

Data processing: Data validation, outlier detection, basic aggregation, and JSON formatting.

Output: Validated and structured biosignal data ready for analysis.

Step 5

Terminal transmits the structured biosignal data to the server, either immediately or in scheduled batches, via an encrypted internet connection (HTTPS).

Input: Validated biosignal dataset.

Data processing: Data packaging, encryption, and secure network transmission.

Output: Biosignal data securely received by the server.

Step 6

Server receives the biosignal data, storing it in a user-profiled database. The server preprocesses the data, applying normalization and trend extraction algorithms.

Input: Received biosignal dataset.

Data processing: Data normalization, trend analysis, and quality control checks.

Output: Preprocessed data vectors representing user physiology and trends.

Step 7

Server generates a prompt sentence using the preprocessed data and current usage context (such as duration of use or reported user need). The server uses this prompt to query the generative AI model, which calculates a user state index and generates a personalized stimulation signal pattern.

Input: Preprocessed biosignal data and user context; prompt sentence (e.g., "Generate an optimal massage program based on HR: 78 bpm, Temp: 36.6° C., GSR: 8 μS for post-desk-work relaxation").

Data processing: Neural network inference with generative model; state index computation; synthesis of stimulation instructions.

Output: Individualized stimulation signal pattern and state index.

Step 8

Server transmits the generated stimulation signal pattern and associated parameters back to the terminal.

Input: Generated stimulation signal pattern.

Data processing: Serialization, integrity verification, and secure network delivery.

Output: Stimulation command package received by the terminal.

Step 9

Terminal parses the received signal pattern and sends corresponding real-time control signals to the control device over the wireless connection.

Input: Stimulation command package.

Data processing: Instruction decoding, scheduling of actuator events, and communication handling.

Output: Real-time actuation commands delivered to the control device.

Step 10

Control device activates the stimulation signal generation device to deliver the specified pattern to the user's body through the wearable garment (e.g., frequency, duration, location of stimulation), enabling the personalized massage.

Input: Actuation commands from the terminal.

Data processing: Real-time digital-to-analog signal conversion and device actuation, with feedback monitoring.

Output: Delivery of physical stimulation to user; ongoing status reporting to terminal.

Step 11

User experiences the massage session as per the individualized pattern and, after completion, is prompted by the terminal to provide feedback. The user enters feedback about the comfort, effectiveness, or particular preferences.

Input: User's subjective evaluation and app input.

Data processing: Feedback entry, formatting, and packaging.

Output: Structured feedback data sent to the terminal.

Step 12

Terminal sends collected user feedback to the server for storage and potential use in future model learning.

Input: Structured feedback data.

Data processing: Data integrity checking and secure transmission.

Output: Feedback stored in user-linked database on server.

Step 13

Server uses accumulated feedback as additional training data to update and refine the generative AI model, improving subsequent personalization and instruction accuracy for future sessions.

Input: Feedback dataset and historical biosignal/command data.

Data processing: Supervised or reinforcement learning processes on the AI model; weight updates; performance evaluation.

Output: Improved generative AI model for future operation.

Application Example 1

Description follows regarding a flow of the specific processing in an Application Example 1. The units of the system described below are implemented by the data processing device 12 and the smart device 14. The data processing device 12 is called a "server" and the smart device 14 is called a "terminal".

In industrial and labor-intensive environments, workers are often required to maintain prolonged standing positions or engage in strenuous activities, resulting in significant physical fatigue. Existing relaxation or massage systems are generally standardized and do not adapt to the real-time physical or emotional state of individual users, which limits their effectiveness in providing optimal personalized relaxation. Furthermore, conventional systems lack the ability to continuously collect user feedback and automatically evolve their operation for improved relaxation effects based on individual user needs.

The specific processing by the specific processing unit 290 of the data processing device 12 in Application Example 1 is realized by the following means.

The present invention provides a server comprising a processor configured to receive biometric information and emotion estimation information from a wearable biometric data acquiring garment via a computing device, analyze the information using a generative artificial intelligence model to determine the user's relaxation and emotional state, generate control commands for a plurality of low-frequency stimulation elements embedded in the garment, transmit the control commands to the computing device for automated execution, and further update the generative artificial intelligence model in response to user feedback, thereby enabling continuous adaptation and optimization of individualized massage programs for enhanced user relaxation. This enables real-time, personalized relaxation support tailored to the physical and emotional status of each user, along with iterative improvement of the system through user feedback.

The term "biometric information" refers to data related to physiological parameters of a user, such as heart rate, body temperature, and skin conductance, that is acquired from the user's body.

The term "biometric data acquiring garment" refers to a wearable item designed to closely fit a user's body and equipped with detection elements and stimulation elements for the purpose of acquiring biometric information and delivering therapeutic effects.

The term "detection element" refers to a sensor embedded in the garment, configured to contact the user's body and measure biometric information such as heart rate, temperature, or conductance.

The term "low-frequency stimulation element" refers to an actuator or electrode embedded in the garment, designed to apply low-frequency electrical pulses to specific areas of the user's body to produce a massage effect.

The term "control unit" refers to an electronic circuit or module that manages the operation and power supply of the detection elements and low-frequency stimulation elements integrated in the garment.

The term "computing device" refers to an external information processing device, such as a smartphone or tablet, capable of wireless communication with the control unit and running software to collect, process, and transmit biometric information.

The term "server" refers to a network-connected information processing apparatus configured to store, analyze, and process biometric and feedback information, and run artificial intelligence models to generate control commands.

The term "generative artificial intelligence model" refers to a machine learning software module implemented on the server, capable of analyzing biometric and emotional information to generate customized massage or stimulation patterns.

The term "control command" refers to an instruction set generated by the server, specifying operational parameters (such as activation timing, intensity, and area) for the low-frequency stimulation elements to administer personalized massage.

The term "experience evaluation information" refers to data representing user feedback regarding the effectiveness, comfort, or user preference of the performed massage program, which is utilized for model learning and system improvement.

The term "presentation device" refers to a user interface apparatus, such as a head-mounted display, smartphone screen, or similar, that is capable of presenting massage information or control command details to the user.

The term "power storage member" refers to a battery or similar device embedded in the control unit which supplies electrical power to the garment's internal components.

One embodiment of the present invention is implemented as a system comprised of a biometric data acquiring garment, a control unit, a computing device, and a server equipped with a generative artificial intelligence model.

The user wears the biometric data acquiring garment, which is designed to fit closely against the body. This garment contains detection elements such as sensors for measuring heart rate, body temperature, and skin conductance, as well as low-frequency stimulation elements to deliver electrical pulses for massage effects. The control unit, installed in the garment, manages the operation and power supply of the detection elements and low-frequency stimulation elements. It is equipped with a power storage member, such as a rechargeable battery, and is capable of wireless communication, such as via Bluetooth Low Energy.

The user interacts with the system using a computing device, such as a smartphone or tablet. The dedicated application, developed using platforms such as Android (Java/Kotlin), iOS (Swift), or a cross-platform solution like Flutter, runs on the computing device. The application wirelessly connects to the garment's control unit and periodically receives biometric data from the detection elements. The computing device temporarily stores the biometric data locally and then securely transmits the data to the server using a protocol such as HTTPS over Wi-Fi or a mobile data network.

The server, which may be realized using commercial cloud computing resources such as a virtual machine or container instance, receives, stores, and analyzes biometric information. The server is configured with an artificial intelligence module, typically implemented using frameworks such as TensorFlow or PyTorch. This module includes a generative artificial intelligence model designed to process the incoming biometric data along with any provided emotional state information (which can be estimated based on facial analysis or voice data forwarded from the computing device). The generative AI model determines the user's current relaxation and emotional state, then generates a control command specifying massage parameters, such as pad activation regions, pulse frequency, intensity, and duration.

The server sends the generated control command to the computing device, which interprets the command and relays specific activation instructions to the garment control unit. Consequently, the control unit automatically operates the low-frequency stimulation elements as specified in the control command, enabling the user to receive a tailored massage program based on their physical and emotional condition in real time.

Following the massage program, the user is prompted through the application to provide experience evaluation information. This can include a satisfaction rating, written feedback, or suggestions for improvement. The computing device transmits this experience evaluation information to the server, which stores the data and utilizes it to retrain or fine-tune the generative AI model, thereby enhancing the degree of personalization for future massage programs.

An example configuration employs a biometric data acquiring garment based on stretchable conductive textiles, an ARM microcontroller for the control unit, Bluetooth Low Energy or Wi-Fi for wireless communication, a smartphone application built with standard mobile development frameworks, a server hosted on a general-purpose cloud service, and generative models constructed using Python and the TensorFlow or PyTorch libraries.

As a specific example, when an industrial worker experiences fatigue from long hours of standing, the system collects the worker's heart rate, skin conductance, and body temperature during a shift via the garment's biometric detection elements. The computing device transfers this data to the server, where the generative AI model processes it together with estimated emotional state (e.g., determined from a brief facial recognition scan). The AI analyzes trends and determines that the worker is experiencing stress and muscular tension in the back and shoulders. The server then outputs a control command to initiate a massage targeting the specified regions with a gentle-to-moderate pulse pattern. The worker experiences this personalized massage on demand during a break, and afterward, uses the application to submit feedback indicating whether they would prefer increased intensity or focus on a different area in the future. The system incorporates this feedback into subsequent session customization.

A representative prompt sentence example for the generative AI model is as follows: "Monitor and analyze the real-time biometric data (heart rate, body temperature, skin conductance) of a factory worker. Based on these readings and the estimated emotional state, generate the most appropriate, personalized massage program to maximize relaxation. Output clear control instructions for the wearable massage device and display program details to the user. Additionally, collect user feedback after the session and adjust the future massage program accordingly."

Through this embodiment, the system facilitates the real-time delivery of personalized, adaptive relaxation programs that continuously improve through the application of generative artificial intelligence and user feedback. All technical components and processing steps are selected and configured so as to efficiently realize the claimed invention.

Figure 12:
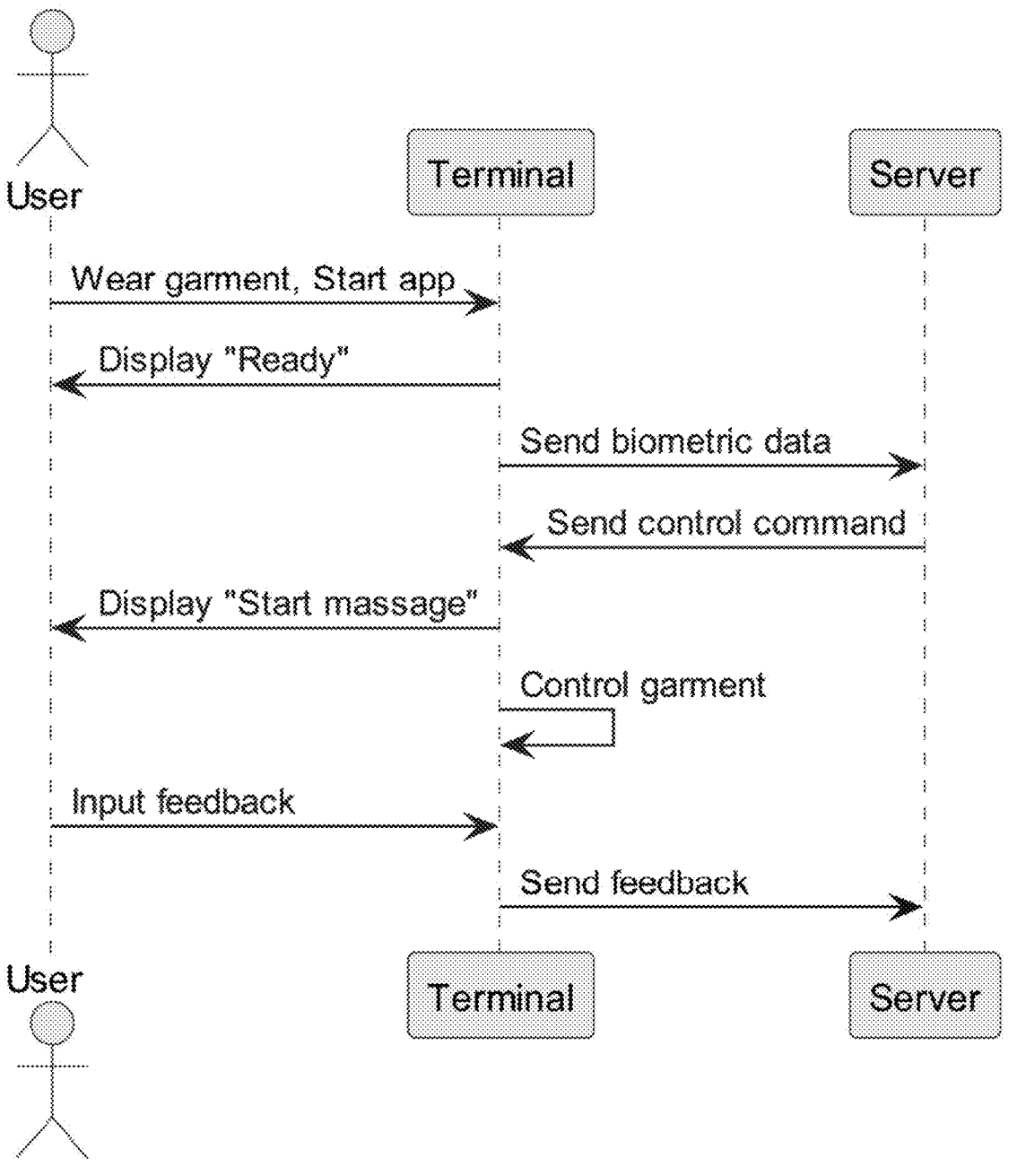
FIG. 12 is a sequence diagram showing the flow of data processing system processing in Application Example 1.

The following describes the processing flow using FIG. 12.

Step 1

User wears the biometric data acquiring garment, which is embedded with detection elements and low-frequency stimulation elements. User turns on the control unit and launches the dedicated application on the computing device.

Input: User operation (wearing garment, activating devices, launching app)

Output: System activation; garment, control unit, and computing device are ready to interact.

Specific action: User presses the power button on the garment's control unit and taps the "Start" button in the application, initiating connectivity routines.

Step 2:

Terminal establishes a wireless connection (such as Bluetooth Low Energy) with the control unit in the garment. Terminal initiates session authentication and status checks.

Input: Bluetooth signal from the control unit, initial handshake request

Output: Confirmation of successful wireless connection and system readiness

Specific action: Terminal scans for available devices, pairs with the control unit, and displays a "Connection Successful" message to the user.

Step 3

Terminal instructs detection elements in the garment to start collecting biometric data (e.g., heart rate, body temperature, skin conductance). Terminal receives sensor readings at regular intervals.

Input: Real-time biometric signals from detection elements

Data processing: Terminal converts analog sensor signals to digital values and timestamps each measurement Output: Digitally formatted biometric data arrays stored transiently in the device's memory Specific action: Terminal initiates a data loop, queries sensors every second, and updates an on-screen dashboard with current readings.

Step 4

Terminal transmits the collected biometric data to the server using a secure protocol (such as HTTPS over Wi-Fi or mobile data).

Input: Digitally formatted biometric data packet

Data processing: Terminal encodes the data in a JSON payload and attaches user identification and timestamps Output: Secure network transmission of biometric data to the server Specific action: Terminal performs a POST request to the cloud endpoint, confirming data upload success on the user interface.

Step 5

Server receives biometric data and, if available, emotion estimation data (such as images or voice samples transferred from the terminal).

Input: Incoming biometric data and emotion estimation data

Data processing: Server parses the received data, verifies data integrity, and stores it in a cloud database; image or audio data is preprocessed for further analysis Output: Clean, structured data entries stored for AI processing Specific action: Server logs data receipt in server logs and updates user session records.

Step 6

Server analyzes the biometric data and emotional state data using the generative AI model. Server calculates a relaxation index and other health indicators.

Input: Cleaned biometric and emotion estimation data from the database

Data processing: Generative AI model performs inference on the latest data to identify user relaxation status and stress factors; the server forms a prompt sentence incorporating all relevant parameters Output: Personalized massage program and corresponding control command Specific action: Server creates a prompt such as "Generate a massage program for user with heart rate 98, body temperature 36.8° C., emotional state 'stressed'," and executes generative model inference.

Step 7

Server transmits the generated control command to the terminal.

Input: Generated massage program and control command

Output: Network transmission of control command to terminal

Specific action: Server sends a JSON response to the terminal, including detailed instructions on target muscle zones, pulse intensity, and session duration.

Step 8

Terminal receives the control command and, based on its content, transmits control instructions to the garment's control unit to activate the designated low-frequency stimulation elements.

Input: Control command From server

Data processing: Terminal parses the massage program parameters and formats them as control signals compatible with the control unit protocol Output: Control signals delivered to the control unit for execution Specific action: Terminal activates a secure Bluetooth channel, sends commands such as "Activate upper back pad, moderate intensity, for 10 minutes," and shows a real-time progress bar in the app.

Step 9

User receives the massage according to the parameters set in the control command.

Input: Physical stimulation from low-frequency pads

Output: Personalized massage experience

Specific action: User feels the massage effect and can monitor remaining time or pause the session via the smartphone application.

Step 10

User is prompted by the terminal (computing device) to provide experience evaluation information at the end of the session, such as a rating or textual feedback.

Input: User inputs feedback via an on-screen form

Output: Feedback data stored temporarily in the terminal and ready for transfer

Specific action: User answers questions like "How satisfied are you?" or enters "I prefer a stronger massage on the back."

Step 11

Terminal transmits the collected experience evaluation information to the server for use in model improvement.

Input: Feedback data from user

Data processing: Terminal formats feedback into a structured JSON payload and sends to server Output: Feedback received and archived for further processing Specific action: Terminal displays "Thank you for your feedback" after successful upload.

Step 12

Server incorporates the experience evaluation information into the learning dataset for the generative AI model. Server optionally triggers re-training or fine-tuning of the model to enhance personalization for future sessions.

Input: New feedback records from multiple users

Data processing: Server updates training data and, on schedule, re-trains or fine-tunes the model parameters Output: Updated generative AI model for personalized massage program generation Specific action: Server logs model update event, and newly generated sessions reflect user feedback for improved experience.

It is also possible to incorporate an emotion engine for estimating the user's emotions. That is, the specific processing unit 290 may estimate the user's emotions using an emotion identification model 59, and perform specific processing based on the estimated emotions.

Example 2

Description follows regarding a flow of the specific processing in an Example 2. The units of the system described below are implemented by the data processing device 12 and the smart device 14. The data processing device 12 is called a "server" and the smart device 14 is called a "terminal".

In modern society, health problems caused by stress and fatigue—particularly among desk workers—are increasing. Conventional relaxation and massage devices are unable to accurately adapt to the unique physiological condition and emotional state of each individual, instead providing uniform programs that cannot maximize relaxation effects. As a result, it remains difficult to deliver personalized, evidence-based relaxation support that reflects both the biometric and emotional status of the user, and to improve the program's effectiveness over time.

The specific processing by the specific processing unit 290 of the data processing device 12 in Example 2 is realized by the following means.

The present invention provides a server comprising a processor configured to acquire biometric data and emotional data from a wearable article in close contact with the user, analyze the biological and emotional state of the user, generate personalized control instruction information for an electrical stimulation unit using a generative information processing algorithm, transmit the control instructions to a control device, receive user evaluation information, and update the subsequent instruction information based on user feedback, with at least the analysis and generation being performed on a cloud network. This enables the provision of highly individualized and adaptive relaxation support programs that optimize stimulation parameters in real-time according to both physical and emotional states of the user, thereby enhancing relaxation effects and continuously improving user experience.

The term "covering article" refers to a wearable material or garment that fits closely to the surface of a user's body and is configured to include embedded biometric information acquisition units and electrical stimulation output units.

The term "biometric information acquisition unit" refers to an electronic module or sensor arranged within the covering article that is capable of detecting and collecting physiological data from the user, such as body temperature, heart rate, or skin conductance.

The term "electrical stimulation output unit" refers to an electronic component embedded within the covering article that delivers electrical signals or currents to the user's body in order to induce muscle stimulation or provide massage effects.

The term "processor" refers to an electronic information processing device, such as a computer, microprocessor, or microcontroller, configured to execute programmed instructions for system operation.

The term "control device" refers to a hardware component connected to the covering article that receives and implements control signals generated by the processor to manage the operation of the electrical stimulation output unit.

The term "biometric data" refers to physiological information, including but not limited to body temperature, heart rate, and skin conductance, acquired from the user by the biometric information acquisition unit.

The term "emotional data" refers to information reflecting the user's emotional state, which may be obtained through analysis of facial expressions, voice tone, biometric variations, or other behavioral and physiological indicators.

The term "generative information processing algorithm" refers to a computational method or artificial intelligence model that generates new control instruction information tailored to the user's current physical and emotional state, based on analysis of received data.

The term "control instruction information" refers to parameter data and commands generated by the processor and intended to specify the operational settings for the electrical stimulation output unit, including output position, intensity, and rhythm.

The term "server device" refers to a computer system or computational resource, typically operating on a cloud network, that hosts and executes at least the analysis and control instruction generation of the present system.

The term "cloud network" refers to a distributed computing infrastructure enabling remote access, storage, and processing of data for the system via the internet.

The term "evaluation information" refers to feedback data provided by the user after use of the system, including subjective assessments or ratings of the relaxation effect, comfort, and suggestions for improvement.

Embodiment for Implementing the Invention

The present invention can be implemented as a system comprising a covering article, such as a wearable garment, a biometric information acquisition unit, an electrical stimulation output unit, a control device, an information processing terminal, and a server device operating on a cloud network. The processor of the server device is configured to analyze biometric and emotional data, generate personalized massage instructions using a generative AI model, and refine future instructions based on user evaluation information.

The covering article is designed to closely fit the user's body surface. Embedded within the covering article are biometric information acquisition units, which may include, for example, a temperature sensor, a heart rate sensor, and a skin conductance sensor. The electrical stimulation output unit may comprise multiple low-frequency pads placed at various positions to deliver adjustable stimulation to the user's muscles. The control device, integrated into the covering article, manages the power supply for these components, typically utilizing a built-in battery, and communicates wirelessly with the information processing terminal via a protocol such as Bluetooth Low Energy (BLE).

The information processing terminal, such as a smartphone or tablet, runs a dedicated application. This application establishes a wireless connection with the control device, acquires and temporarily stores signals from the biometric information acquisition unit, and collects emotional data through image or audio analysis. For this purpose, the application can utilize general-purpose software modules for image analysis, such as OpenCV, or emotion recognition libraries, such as commercially available SDKs for emotion estimation.

The terminal regularly transmits aggregated biometric and emotional data to the server device, which is hosted on a cloud network. The server executes software components including a generative AI model, which may be implemented, for example, using a machine learning framework such as TensorFlow or PyTorch. The server utilizes these models to analyze the user's current physical and emotional states, estimate a relaxation index, and generate optimal control instruction information for the electrical stimulation output unit. For emotion analysis, the server may utilize emotion analysis algorithms based on facial image or vocal intonation extraction, which can be implemented on the cloud using standard emotion recognition packages.

Once generated, the control instruction information is provided to the terminal, which transmits corresponding commands to the control device in the covering article. The control device then operates the electrical stimulation output unit according to the personalized parameters specified by the server, including position, intensity, and rhythm of stimulation.

Following a massage session, the terminal prompts the user to submit subjective evaluation information, such as ratings of massage effectiveness or comfort and suggestions for improvement. This evaluation is uploaded to the server. The server, using its generative AI model, incorporates feedback into future instruction generation, thus enabling adaptive and highly individualized optimization of the massage program for each user.

A specific example of system usage is as follows. The user dons the smart garment and activates the application on their smartphone. The application collects biometric and emotional signals, which are transmitted to the cloud-based server device. The server analyzes these signals and generates a massage program tailored to the user's condition, specifying detailed settings for each electrical pad. The smartphone communicates these settings to the garment, and the user experiences a customized massage while working. After the session, the user provides feedback via the app, and the server updates its personalization algorithms accordingly.

For example, the following prompt sentence may be used when invoking the generative AI model on the server:

"Analyze the user's biophysical data (body temperature, heart rate, skin conductance) and emotional data (facial expressions, voice tone, body temperature changes) to evaluate the relaxation state and generate the optimal massage program. Specify the settings for low-frequency pad position, intensity, and rhythm suitable for the current user state."

Through this configuration, the system continuously adapts to the user's physiological and emotional status, supports highly individualized relaxation programs, and improves its performance iteratively based on user-supplied evaluation information.

Figure 13:
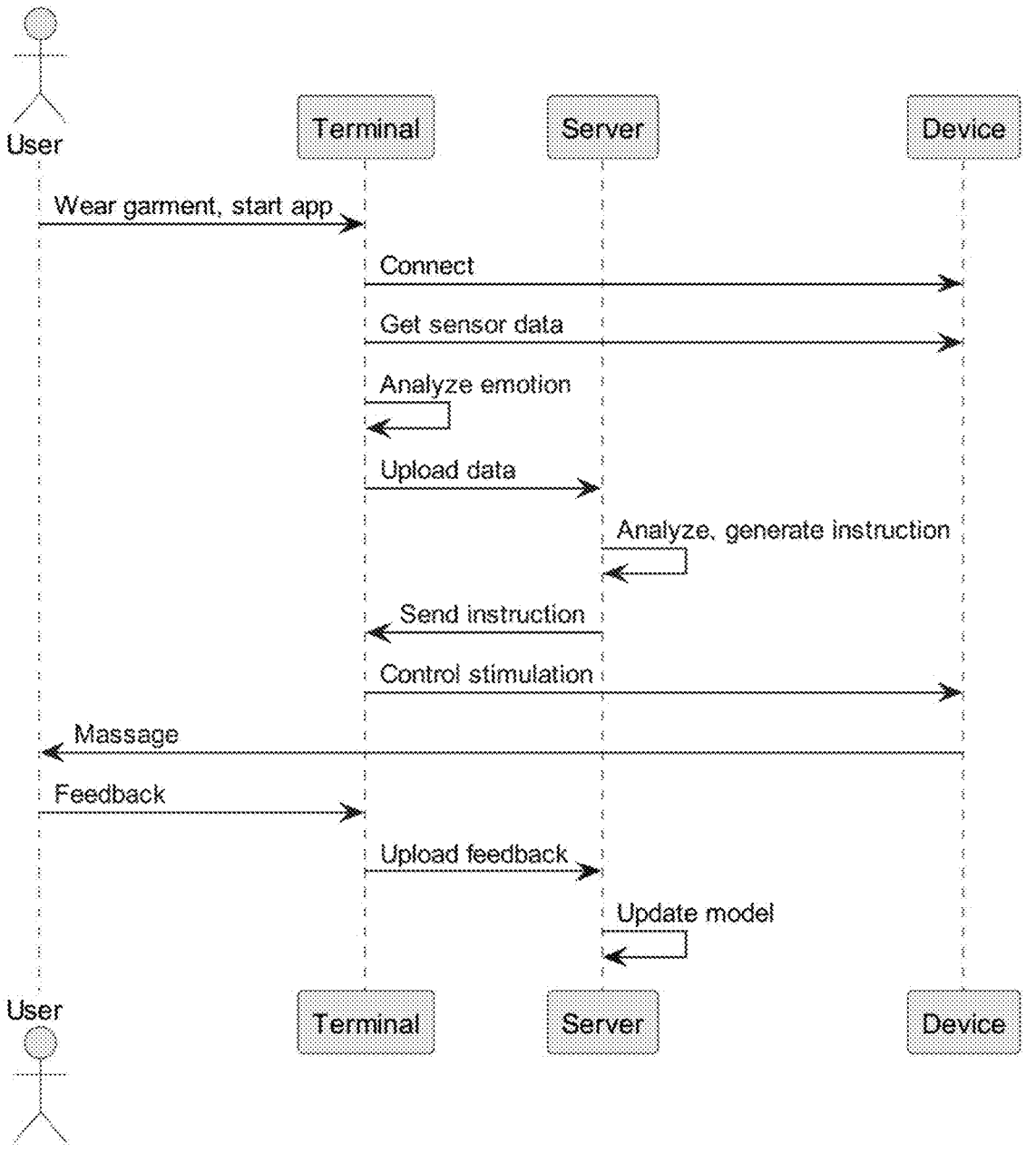
FIG. 13 is a sequence diagram showing the flow of data processing system processing in Example 2.

The following describes the processing flow using FIG. 13.

Step 1
  User wears the covering article equipped with biometric sensors and electrical stimulation pads. User launches the dedicated application on the terminal and activates the control device integrated within the garment.
  Input: User's body, initial application start
  Operation: User ensures the garment fits snugly and verifies connection status on the application interface.
  Output: Physical contact established between user and sensors, application and control device activated Step 2
  Terminal establishes a wireless connection, such as Bluetooth Low Energy, with the control device inside the garment. Terminal confirms the connection and displays status to the user.

Input: Device pairing data, status signals from the control device
  Operation: Terminal scans for nearby approved devices, authenticates the control device, and sets up encrypted communication.
  Output: Secure wireless communication link is established between terminal and control device Step 3
  Terminal starts collecting biometric data, including body temperature, heart rate, and skin conductance, at preset intervals through the biometric information acquisition units within the garment.
  Input: Sensor readings from inside the garment
  Operation: Terminal reads raw sensor signals, preprocesses data by filtering out noise, timestamps each reading, and temporarily stores the aggregated data.
  Output: Processed biometric data stored in terminal memory Step 4
  Terminal acquires emotional data by capturing facial images or recording voice (if permitted by the user) and applies emotion recognition algorithms (such as facial expression or voice tone analysis) to determine the user's emotional state.
  Input: Camera images, microphone audio
  Operation: Terminal extracts facial feature vectors or audio features, processes them using embedded emotion recognition software, and generates emotion classification results.
  Output: Emotional indicators such as emotion labels or scores Step 5
  Terminal aggregates recent biometric data and emotional indicators into a data packet with associated time stamps. Terminal securely uploads this packet to the server device on a cloud network at predefined intervals.
  Input: Processed biometric data, emotional data, session metadata
  Operation: Terminal creates a structured data packet, ensures data encryption, and initiates HTTPS POST to the server API endpoint.
  Output: Data packet successfully transmitted to the server Step 6
  Server receives biometric and emotional data from the terminal. Server stores incoming data in a user-associated database and prepares the data for analysis.
  Input: Uploaded data packet
  Operation: Server verifies packet integrity, authenticates user identity, parses the data, and stores structured records into a secure database.
  Output: Biometric and emotional data stored in cloud database Step 7
  Server analyzes the uploaded data using a machine learning or generative AI model. Server calculates the user's current biological and emotional state, derives a relaxation index, and generates a prompt sentence for the generative AI model.
  Input: Stored biometric and emotional data
  Operation: Server normalizes the input data, extracts relevant features, applies AI-based analysis models, calculates relaxation scores, and formulates an instruction prompt for the generative AI model based on the user's state.

Output: Relaxation index and AI prompt sentence gener-
ated

Step 8

Server generates optimized control instruction informa-
tion for the electrical stimulation output unit by apply-
ing the generative AI model in response to the prompt
sentence.

Input: Prompt sentence, current user state data

Operation: Server inputs the prompt sentence to the
generative AI model, which outputs control parameters
such as pad position, intensity, and rhythm, tailored to
the user. Output: Personalized control instruction infor-
mation Step 9

Server transmits the generated control instruction infor-
mation to the terminal. Terminal converts the received
instruction information into commands compatible
with the control device's protocol.

Input: Control instruction information from the server

Operation: Terminal receives instructions, parses param-
eter values, and packages them into control commands
suitable for the BLE communication protocol.

Output: Ready-to-transmit device commands

Step 10

Terminal sends the commands to the control device,
which drives the electrical stimulation output unit
according to the specified settings.

Input: Device commands from terminal

Operation: Control device activates the required pads,
applies electrical stimulation according to position,
intensity, and rhythm specifications.

Output: Electrical stimulation provided to the user as a
personalized massage

Step 11

User experiences the electrical stimulation session and,
after the session, provides subjective evaluation infor-
mation through a feedback interface in the application.

Input: User's experience of the session

Operation: User enters ratings, comments, or suggestions
within the feedback form presented by the terminal
application.

Output: Evaluation information collected by the terminal

Step 12

Terminal uploads the evaluation information to the server
to enable further personalization.

Input: User evaluation data

Operation: Terminal encrypts and transmits the feedback
data to the server's designated feedback endpoint.

Output: Feedback data recorded in the server's database

Step 13

Server incorporates the new evaluation information and
the historical database to refine the generative AI model
or update its control instruction generation algorithm
for future sessions.

Input: User feedback, prior data history

Operation: Server performs retraining or model fine-
tuning with recent session data and user feedback to
improve future instruction personalization.

Output: Updated generative AI model or parameters for
enhanced personalization in subsequent sessions

Application Example 2

Description follows regarding a flow of the specific
processing in an Application Example 2. The units of the
system described below are implemented by the data processing device 12 and the smart device 14. The data pro-
cessing device 12 is called a "server" and the smart device
14 is called a "terminal".

In traditional relaxation, esthetic, and massage services, it
is difficult to provide an optimal treatment program tailored
to each individual's physiological and emotional state, as the
degree of relaxation and user satisfaction depends heavily on
the staff's experience and intuition. Furthermore, conven-
tional systems cannot acquire and analyze real-time biologi-
cal and emotional data with sufficient accuracy, nor can they
automatically optimize the treatment program based on
individual feedback and biological reactions. This results in
inconsistent treatment quality and limits the ability to con-
tinuously improve user-specific effectiveness.

The specific processing by the specific processing unit
290 of the data processing device 12 in Application Example
2 is realized by the following means.

The present invention provides a server comprising a
processor configured to acquire time-series biological infor-
mation from an individual through a wearable biological
information acquisition medium, analyze the individual's
physiological and emotional state using artificial intelli-
gence, generate an individually customized treatment pro-
gram using a generative artificial intelligence model based
on the analyzed data, control a physical stimulation medium
according to the generated program, receive and analyze
feedback information from the individual after treatment,
and continuously optimize the generation logic for the
treatment program by machine learning. This enables accu-
rate real-time analysis of both biological and emotional data,
automatic generation and execution of personalized treat-
ment routines, and continual refinement of treatment effec-
tiveness based on user feedback, resulting in highly indi-
vidualized and improved relaxation experiences.

The term "biological information acquisition medium"
refers to a wearable article or apparatus that is designed to
come into close contact with an individual's body and is
equipped with one or more sensors for detecting biological
signals, such as body temperature, heart rate, or skin con-
ductance.

The term "biological information" refers to physiological
data acquired from an individual, including but not limited
to heart rate, body temperature, skin conductance, or any
other measurable signals reflecting the individual's physical
state.

The term "physical stimulation medium" refers to a
device or component, such as a low-frequency pad or
actuator, capable of applying controlled physical stimuli
(e.g., electrical, vibrational, or pressure-based stimulation)
to an individual's body for therapeutic or relaxation pur-
poses.

The term "control unit" refers to an electronic module
embedded within or connected to the biological information
acquisition medium, which manages the operation of sen-
sors and physical stimulation media, processes input and
output signals, and communicates wirelessly with an infor-
mation processing device.

The term "information processing device" refers to a
general-purpose or dedicated computing device, such as a
mobile terminal, smartphone, tablet, or server, that is con-
figured to receive, store, process, and transmit data associ-
ated with the biological information acquisition medium and
its components.

The term "artificial intelligence" refers to computational
methods and algorithms that enable data analysis, feature extraction, state estimation, and decision-making based on acquired data, including but not limited to machine learning models and neural networks.

The term "generative artificial intelligence model" refers to a software module or algorithm capable of creating new content, such as a personalized treatment program, based on input data or instructions, including prompt-based content creation utilizing generative models.

The term "treatment program" refers to a structured set of control instructions specifying parameters of physical stimulation, such as position, intensity, rhythm, and timing, generated to optimize the individual's relaxation or therapeutic experience.

The term "feedback information" refers to data input by the individual after receiving treatment, including subjective ratings, comments, preferences, or other information pertaining to the treatment experience.

The term "machine learning" refers to a subfield of artificial intelligence that involves the use of algorithms and statistical models to enable computational systems to improve their performance on a specific task through continuous accumulation and analysis of data and feedback.

The term "prompt sentence" refers to a text-based instruction, explanation, or command provided to a generative artificial intelligence model in order to guide or specify the process and logic of treatment program generation.

An embodiment for carrying out the present invention is described below. A user wears a biological information acquisition medium, which takes the form of a full-body, close-fitting garment equipped with embedded sensors and physical stimulation media such as low-frequency pads. The sensors are configured to measure biological information including, but not limited to, heart rate, body temperature, and skin conductance. The control unit, embedded in the garment or connected externally, governs the operation of the sensors and the physical stimulation medium. The control unit contains a battery to provide operating power and is capable of wireless communication, for example, utilizing Bluetooth Low Energy (BLE).

The user operates an information processing device, such as a smartphone or tablet, which executes a dedicated application. The application wirelessly connects to the garment's control unit. When the user activates the system, the terminal collects real-time biological information from the sensors through the control unit. The collected data is temporarily stored on the internal memory of the terminal and is visually displayed to the user via the application interface. The software may be designed in platforms such as iOS or Android, and common programming environments include Swift, Kotlin, or React Native for the interface. For wireless communication, libraries supporting Bluetooth (such as CoreBluetooth or Android Bluetooth API) are used.

The terminal transmits the time-series biological data to a server, typically a cloud computing resource (such as an EC2 instance on a commercial cloud service). The server is equipped with artificial intelligence modules implemented, for example, in Python with libraries like scikit-learn and TensorFlow, which perform preprocessing (such as outlier removal and smoothing) and feature extraction of the received data. The artificial intelligence module analyzes the data to estimate the user's relaxation index and, using additional emotion analysis engines (for example, models from Huggingface transformers), determines the user's emotional state. The server then uses a generative artificial intelligence model to automatically generate an optimal treatment program tailored for the user. This includes decisions on physical stimulation parameters: the position, intensity, and rhythm of the low-frequency pads.

The server formats the treatment program and sends it back as a control signal to the terminal. On receipt, the terminal relays the control signal to the garment's control unit. The control unit activates the physical stimulation medium according to the received instructions, thereby executing the treatment program on the user's body.

After the treatment, the user provides feedback through the application, which may include rating, comments, and textual or voice input describing their experience. The terminal transmits this feedback along with post-treatment biological data back to the server. The server analyzes the feedback using natural language processing engines (such as spaCy or BERT-based models) to extract user preferences and satisfaction metrics. The machine learning module incorporates this information to further refine and optimize the generative model parameters for subsequent sessions.

For example, if the feedback indicates that the user felt insufficient intensity at the shoulders, the system will adjust future treatment programs to increase stimulation in the relevant area. Continuous learning from historical data and user-specific feedback ensures persistent improvement and individualization of the treatment.

A concrete prompt sentence example used to instruct the generative AI model is: "Based on user biometric data (heart rate: 72 bpm, body temp: 36.2° C., skin conductance: 8.9 μS) and text feedback ('I feel a bit anxious today'), generate a treatment program optimizing relaxation in the lower back area."

Through this embodiment, it is possible for a user to receive real-time, personalized, and optimized treatment using an automated system that integrates wearable hardware, wireless communication, and advanced artificial intelligence, while continuously learning from feedback to enhance user experience.

Figure 14:
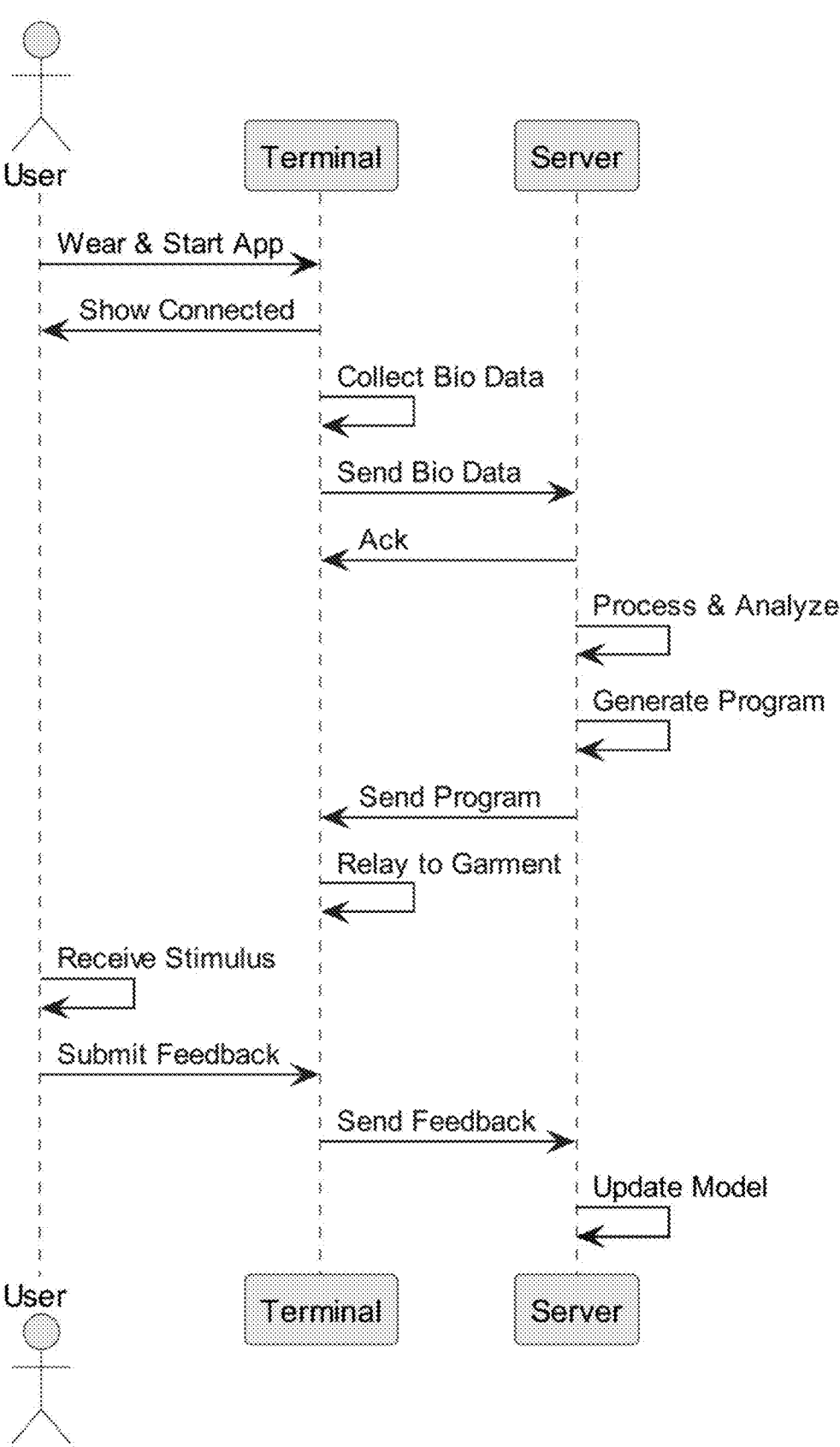
FIG. 14 is a sequence diagram showing the flow of data processing system processing in Application Example 2.

The following describes the processing flow using FIG. 14.

Step 1

User wears the wearable biological information acquisition medium (full-body garment with embedded sensors and stimulation pads) and activates the control unit.

Input: User's physical presence and interaction.

Output: Sensors and control unit are powered on and initialized for data transmission.

User ensures the garment fits securely, presses the power button on the control unit, and confirms device readiness via an indicator light.

Step 2

Terminal establishes wireless (Bluetooth) connection with the control unit and launches the dedicated application.

Input: Signal from the control unit requesting a connection.

Output: Secure, paired communication link and application interface displayed to user.

Terminal scans for available Bluetooth devices, authenticates the connection, and shows a "Connected" status on the app interface.

Step 3

Terminal collects real-time biological information from the sensors via the control unit.

Input: Sensor signal data (e.g., heart rate, body temperature, skin conductance).

Output: Temporarily stored time-series biological data in terminal memory and real-time display on the application.

Terminal polls each sensor at intervals (e.g., every second), logs values in a dataset, and updates the UI to show current readings.

Step 4

Terminal transmits biological data to the server through a secure (HTTPS) internet connection.

Input: Time-series biological data stored in terminal memory.

Output: Data packets sent to the server and receipt confirmation.

Terminal formats data as JSON objects, establishes an HTTPS session, and sends batches of readings to the server endpoint.

Step 5

Server preprocesses received biological data (smoothing, filtering, outlier removal) and extracts relevant features.

Input: Raw time-series biological data received from terminal.

Output: Cleaned and normalized biological data, along with calculated features used for AI analysis.

Server parses data, applies preprocessing algorithms like moving average, removes noise, and computes statistical features such as mean heart rate and skin conductance trend.

Step 6

Server analyzes processed biological data using artificial intelligence and calculates the user's relaxation index, while also analyzing emotional state using additional data (e.g., user comments or voice).

Input: Preprocessed biological data and, if present, emotion-related input.

Output: Numeric relaxation index and identified emotional state for the current session.

Server applies machine learning models (e.g., RandomForestClassifier in scikit-learn) for relaxation assessment, and uses an emotion recognition model for text or voice data to generate a session profile.

Step 7

Server generates a personalized treatment program using a generative AI model, based on the relaxation index and emotional state.

Input: Relaxation index, emotional state, and extracted features from the previous step.

Output: Structured treatment program specifying physical stimulus location, intensity, rhythm, and duration.

Server provides this data as a control signal and constructs an explanatory prompt sentence for model interpretability.

Step 8

Server sends the treatment program to the terminal.

Input: Treatment program data as control signal.

Output: Received treatment program on the terminal, displayed to user for confirmation if necessary.

Terminal parses the incoming JSON object and shows a summary ("Back massage, intensity 70, rhythm pulse, duration 12 minutes") on the app.

Step 9

Terminal relays the treatment program to the control unit, which actuates the physical stimulation medium according to the prescribed instructions.

Input: Commands for pad activation, intensity, and rhythm.

Output: Activation of physical stimulation pads and execution of the treatment on the user's body.

Control unit interprets the commands, signals pads to begin stimulation at the defined settings, and logs operation for session tracking.

Step 10

User experiences the treatment and provides feedback after the session via the application interface (e.g., ratings, comments, voice messages).

Input: User post-session interaction and feedback entry.

Output: Feedback data recorded in terminal memory and available for upload.

User rates the session on a scale, selects areas needing improvement, and adds a typed comment or voice memo.

Step 11

Terminal uploads feedback data and post-session biological data to the server.

Input: User feedback data and current biological data.

Output: Data packets securely transmitted to the server for further analysis.

Terminal batches feedback, attaches corresponding biological data (e.g., change in heart rate), and sends everything to the server via HTTPS.

Step 12

Server analyzes feedback and updated biological data using natural language processing and machine learning techniques, and updates the generative AI model parameters to further personalize future treatment programs.

Input: Feedback information and biological data across multiple sessions for the user.

Output: Adapted generative AI model and improved future treatment program logic.

Server extracts key preferences and sentiment from the feedback, retrains personalization algorithms, and stores adjustment factors for the individual user profile.

The data generation model 58 is a so-called generative artificial intelligence (AI). Examples of the data generation model 58 include generative AIs such as ChatGPT (registered trademark) (Internet search <URL: https://openai.com/blog/chatgpt>) and the like. The data generation model 58 is obtained by performing deep learning with a neural network. The data generation model 58 is input with a prompt including an instruction, and is input with inference data such as audio data representing speech, text data representing text, image data representing images (for example, still image data or video data), and the like. The data generation model 58 takes the input inference data, performs inference according to the instruction indicated in the prompt, and outputs an inference result in one or more data format from out of audio data, text data, image data, or the like. The data generation model 58 includes, for example, a text generative AI, an image generative AI, a multimodal generative AI, or the like. Reference here to inference indicates, for example, analysis, classification, prediction, and/or abstraction etc. The specific processing unit 290 performs the specific processing referred to above while using the data generation model 58. The data generation model 58 may be a model fine-tuned so as to output an inference result from a prompt not including an instruction, and in such cases the data generation model 58 is able to output an inference result from the prompt not including an instruction. There are plural types of the data generation model 58 included in the data processing device 12 or the like, and the data generation models 58 include an AI other than a generative AI. An AI other than a generative AI is, for example, a linear regression, a logistic regression, a decision tree, a random forest, a support vector machine (SVM), a k-means clustering, a convolutional neural network (CNN), a recurrent neural network (RNN), a generative adversarial network (GAN), a naïve Bayes, or the like and is capable of performing various processing, however there is no limitation to such examples. The AI may be an AI agent. Moreover, when the processing of each of the units mentioned above is performed by an AI, this processing is partly or entirely performed by the AI, however there is no limitation to such examples. Moreover, processing executed by an AI including a generative AI may be switched to rule-based processing, and rule-based processing may be switched to processing executed by an AI including a generative AI.

Moreover, although the processing by the data processing system 10 described above was executed by the specific processing unit 290 of the data processing device 12 or by the control unit 46A of the smart device 14, the processing may be executed by a specific processing unit 290 of the data processing device 12 and a control unit 46A of the smart device 14. Moreover, the specific processing unit 290 of the data processing device 12 acquires and collects information needed for processing from the smart device 14 or from an external device or the like, and the smart device 14 acquires and collects information needed for processing from the data processing device 12 or from an external device or the like.

For example, a collection unit is implemented by the control unit 46A of the smart device 14 and/or by the specific processing unit 290 of the data processing device 12. For example, an acquisition unit acquires number-of-steps data using the camera 42 and/or the communication I/F 44 of the smart device 14, and the number-of-steps data is processed by the specific processing unit 290 of the data processing device 12. For example, an analysis unit implemented by the specific processing unit 290 of the data processing device 12 analyzes data from the collection unit and the acquisition unit. For example, a generation unit implemented by the specific processing unit 290 of the data processing device 12 generates a cooking menu using a generative AI. For example, a supply unit implemented by the output device 40 of the smart device 14 and/or the specific processing unit 290 of the data processing device 12 supplies the generated cooking menu to the user. Correspondence relationships of each unit to devices and control units are not limited to the examples described above, and various modifications thereof are possible.

The above exemplary embodiment gives an implementation example in which the specific processing is performed by the data processing device 12, however technology disclosed herein is not limited thereto, and the specific processing may be performed by the smart device 14.

Second Exemplary Embodiment

Figure 3:
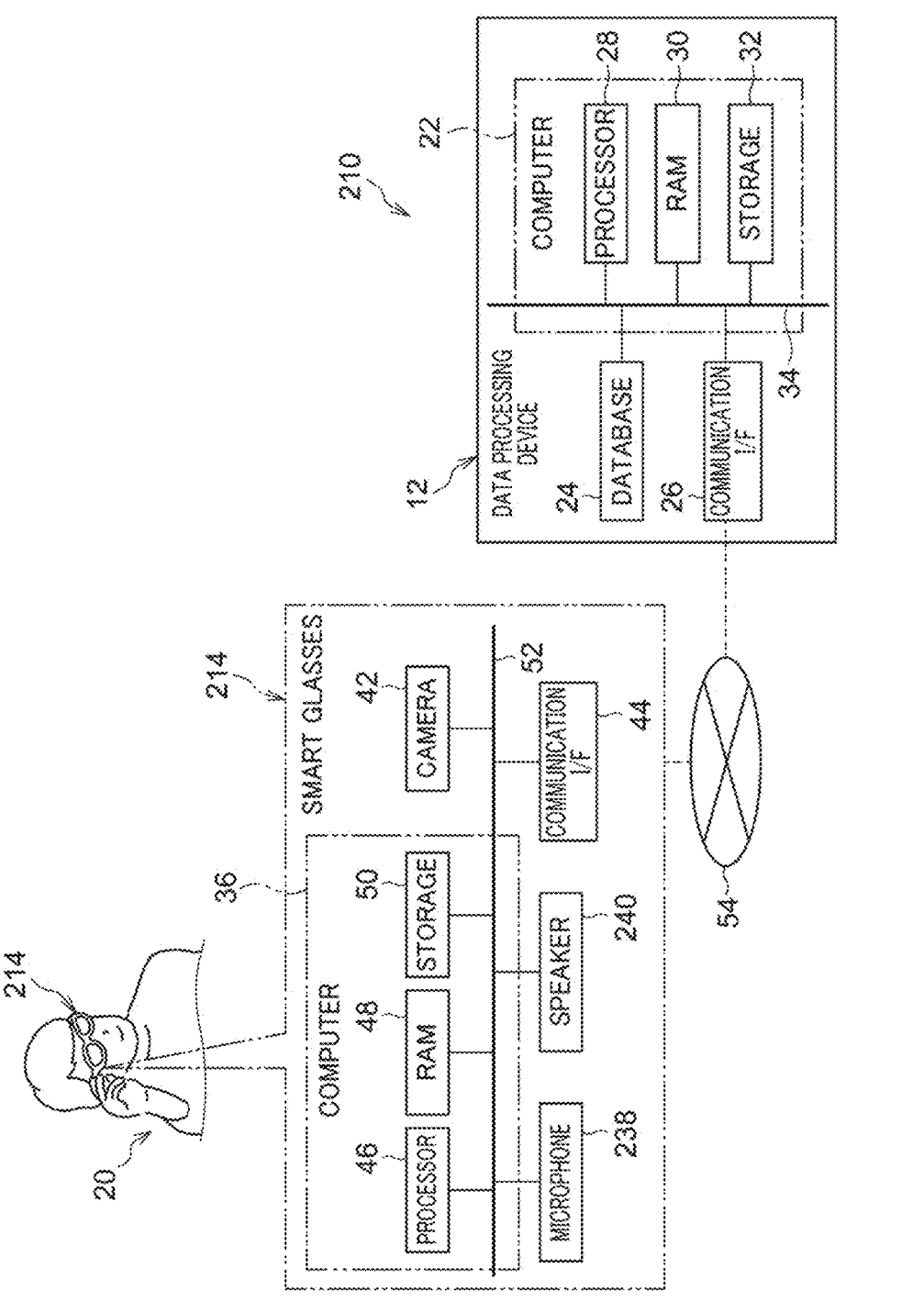
FIG. 3 is a schematic diagram illustrating an example of a configuration of a data processing system according to a second exemplary embodiment.

FIG. 3 illustrates an example of a configuration of a data processing system 210 according to a second exemplary embodiment.

As illustrated in FIG. 3, the data processing system 210 includes a data processing device 12 and smart glasses 214. A server is an example of the data processing device 12.

The data processing device 12 includes a computer 22, a database 24, and a communication I/F 26. The computer 22 is an example of a "computer" according to technology disclosed herein. The computer 22 includes a processor 28, RAM 30, and storage 32. The processor 28, the RAM 30, and the storage 32 are connected to a bus 34. The database 24 and the communication I/F 26 are also connected to the bus 34. The communication I/F 26 is connected to a network

54. Examples of the network 54 include a Wide Area Network (WAN) and/or a local area network (LAN).

The smart glasses 214 include a computer 36, a microphone 238, a speaker 240, a camera 42, and a communication I/F 44. The computer 36 includes a processor 46, RAM 48, and storage 50. The processor 46, the RAM 48, and the storage 50 are connected to a bus 52. The microphone 238, the speaker 240, the camera 42, and the communication I/F 44 are also connected to the bus 52.

The microphone 238 receives an instruction or the like from a user 20 by receiving speech uttered by the user 20. The microphone 238 captures the speech uttered by the user 20, converts the captured speech into audio data, and outputs the audio data to the processor 46. The speaker 240 outputs audio under instruction from the processor 46.

The camera 42 is a compact digital camera installed with an optical system such as a lens, an aperture, a shutter, and the like, and with an imaging device such as a complementary metal-oxide semiconductor (CMOS) image sensor or a charge coupled device (CCD) image sensor or the like. The camera 42 images the surroundings of the user 20 (for example, an imaging range defined by an angle of view equivalent to the width of visual field of an ordinary healthy subject).

The communication I/F 44 is connected to the network 54. The communication I/F 44 and the communication I/F 26 perform the role of exchanging various information between the processor 46 and the processor 28 over the network 54. The exchange of various information between the processor 46 and the processor 28 is performed in a secure state using the communication I/F 44 and the communication I/F 26.

Figure 4:
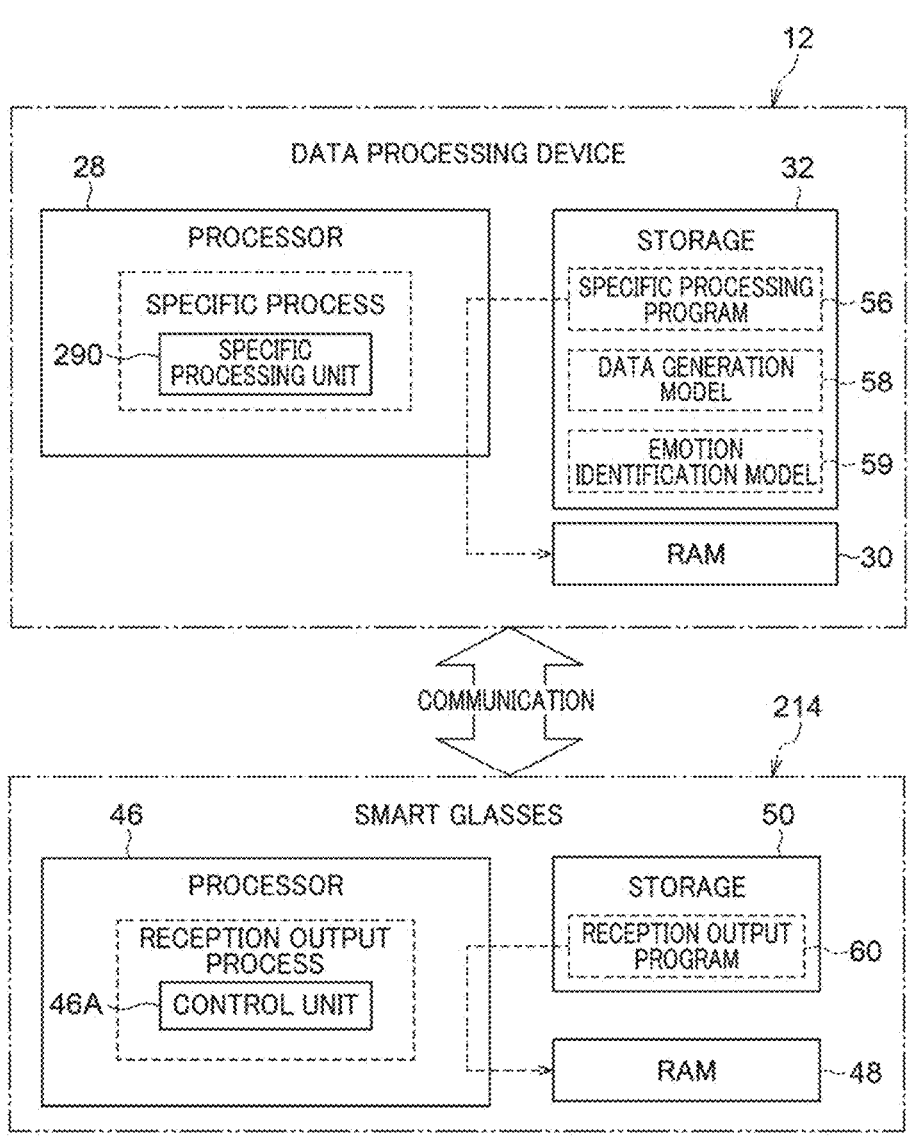
FIG. 4 is a schematic diagram illustrating an example of relevant functions of a data processing device and smart glasses according to the second exemplary embodiment.

FIG. 4 illustrates an example of relevant functions of the data processing device 12 and the smart glasses 214. As illustrated in FIG. 4, specific processing is performed by the processor 28 in the data processing device 12. A specific processing program 56 is stored in the storage 32.

The specific processing program 56 is an example of a "program" according to technology disclosed herein. The processor 28 reads the specific processing program 56 from the storage 32, and in the RAM 30 executes the read specific processing program 56. The specific processing is implemented by the processor 28 operating as the specific processing unit 290 according to the specific processing program 56 executed in the RAM 30.

The data generation model 58 and the emotion identification model 59 are stored in the storage 32. The data generation model 58 and the emotion identification model 59 are employed by the specific processing unit 290. The specific processing unit 290 uses the emotion identification model 59 to estimate an emotion of a user, and is able to perform the specific processing using the user emotion. In an emotion estimation function (emotion identification function) that uses the emotion identification model 59, various estimations, predictions, and the like are performed related to emotions of the user, include estimating and predicting the emotion of the user, however, there is no limitation to such examples. Moreover, estimation and prediction of emotion also includes, for example, analyzing (parsing) emotions and the like.

Reception and output processing is performed by the processor 46 in the smart glasses 214. A reception and output program 60 is stored in the storage 50. The processor 46 reads the reception and output program 60 from the storage 50 and in the RAM 48 executes the read reception and output program 60. The reception and output processing is implemented by the processor 46 operating as the control unit 46A according to the reception and output program 60 executed in the RAM 48. Note that a configuration may be adopted in which the smart glasses 214 include a data generation model and an emotion identification model similar to the data generation model 58 and the emotion identification model 59, and processing similar to the specific processing unit 290 is performed using these models.

Next, description follows regarding the specific processing by the specific processing unit 290 of the data processing device 12. The units of the system described below are implemented by the data processing device 12 and the smart glasses 214. In the following description the data processing device 12 is called a "server", and the smart glasses 214 is called a "terminal".

Example 1

Explanation of flow will be omitted due to being similar to a flow of the specific processing in Example 1 as described in the first exemplary embodiment above.

Application Example 1

Explanation of flow will be omitted due to being similar to a flow of the specific processing in Application Example 1 as described in the first exemplary embodiment above.

Example 2

Explanation of flow will be omitted due to being similar to a flow of the specific processing in Example 2 as described in the first exemplary embodiment above.

Application Example 2

Explanation of flow will be omitted due to being similar to a flow of the specific processing in Application Example 2 as described in the first exemplary embodiment above.

The specific processing unit 290 transmits a result of the specific processing to the smart glasses 214. The control unit 46A in the smart glasses 214 outputs the specific processing result to the speaker 240. The microphone 238 acquires audio representing user input in response to the specific processing result. The control unit 46A transmits audio data representing the user input as acquired by the microphone 238 to the data processing device 12. The specific processing unit 290 in the data processing device 12 acquires the audio data.

The data generation model 58 is a so-called generative artificial intelligence (AI). Examples of the data generation model 58 include generative AIs such as ChatGPT (registered trademark) (Internet search <URL: https://openai.com/blog/chatgpt>) and the like. The data generation model 58 is obtained by performing deep learning with a neural network. The data generation model 58 is input with a prompt including an instruction, and is input with inference data such as audio data representing speech, text data representing text, image data representing images (for example, still image data or video data), and the like. The data generation model 58 takes the input inference data, performs inference according to the instruction indicated in the prompt, and outputs an inference result in one or more data format from out of audio data, text data, image data, or the like. The data generation model 58 includes, for example, a text generative AI, an image generative AI, a multimodal generative AI, or the like. Reference here to inference indicates, for example, analysis, classification, prediction, and/or abstraction etc. The specific processing unit 290 performs the specific processing referred to above while using the data generation model 58. The data generation model 58 may be a model fine-tuned so as to output an inference result from a prompt not including an instruction, and in such cases the data generation model 58 is able to output an inference result from the prompt not including an instruction. There are plural types of the data generation model 58 included in the data processing device 12 or the like, and the data generation models 58 include an AI other than a generative AI. An AI other than a generative AI is, for example, a linear regression, a logistic regression, a decision tree, a random forest, a support vector machine (SVM), a k-means clustering, a convolutional neural network (CNN), a recurrent neural network (RNN), a generative adversarial network (GAN), a naïve Bayes, or the like and is capable of performing various processing, however there is no limitation to such examples. The AI may be an AI agent. Moreover, when the processing of each of the units mentioned above is performed by an AI, this processing is partly or entirely performed by the AI, however there is no limitation to such examples. Moreover, processing executed by an AI including a generative AI may be switched to rule-based processing, and rule-based processing may be switched to processing executed by an AI including a generative AI.

Although the processing by the data processing system 10 described above is executed by the specific processing unit 290 of the data processing device 12 or by the control unit 46A of the smart glasses 214, the processing may be executed by a specific processing unit 290 of the data processing device 12 and a control unit 46A of the smart glasses 214. Moreover, the specific processing unit 290 of the data processing device 12 acquires and collects information needed for processing from the smart glasses 214 or from an external device or the like, and the smart glasses 214 acquires and collects information needed for processing from the data processing device 12 or from an external device or the like.

For example, the collection unit is implemented by the control unit 46A of the smart glasses 214 and/or by the specific processing unit 290 of the data processing device 12. For example, an acquisition unit acquires number-of-steps data using the camera 42 and/or the communication I/F 44 of the smart glasses 214, and the number-of-steps data is processed by the specific processing unit 290 of the data processing device 12. For example, an analysis unit implemented by the specific processing unit 290 of the data processing device 12 analyzes data from the collection unit and the acquisition unit. For example, a generation unit implemented by the specific processing unit 290 of the data processing device 12 generates a cooking menu using a generative AI. For example, a supply unit implemented by the speaker 240 of the smart glasses 214 and/or the specific processing unit 290 of the data processing device 12 supplies the generated cooking menu to the user. Correspondence relationships of each unit to devices and control units are not limited to the examples described above, and various modifications thereof are possible.

The above exemplary embodiment gives an implementation example in which the specific processing is performed by the data processing device 12, however technology disclosed herein is not limited thereto, and the specific processing may be performed by the smart glasses 214.

Third Exemplary Embodiment

Figure 5:
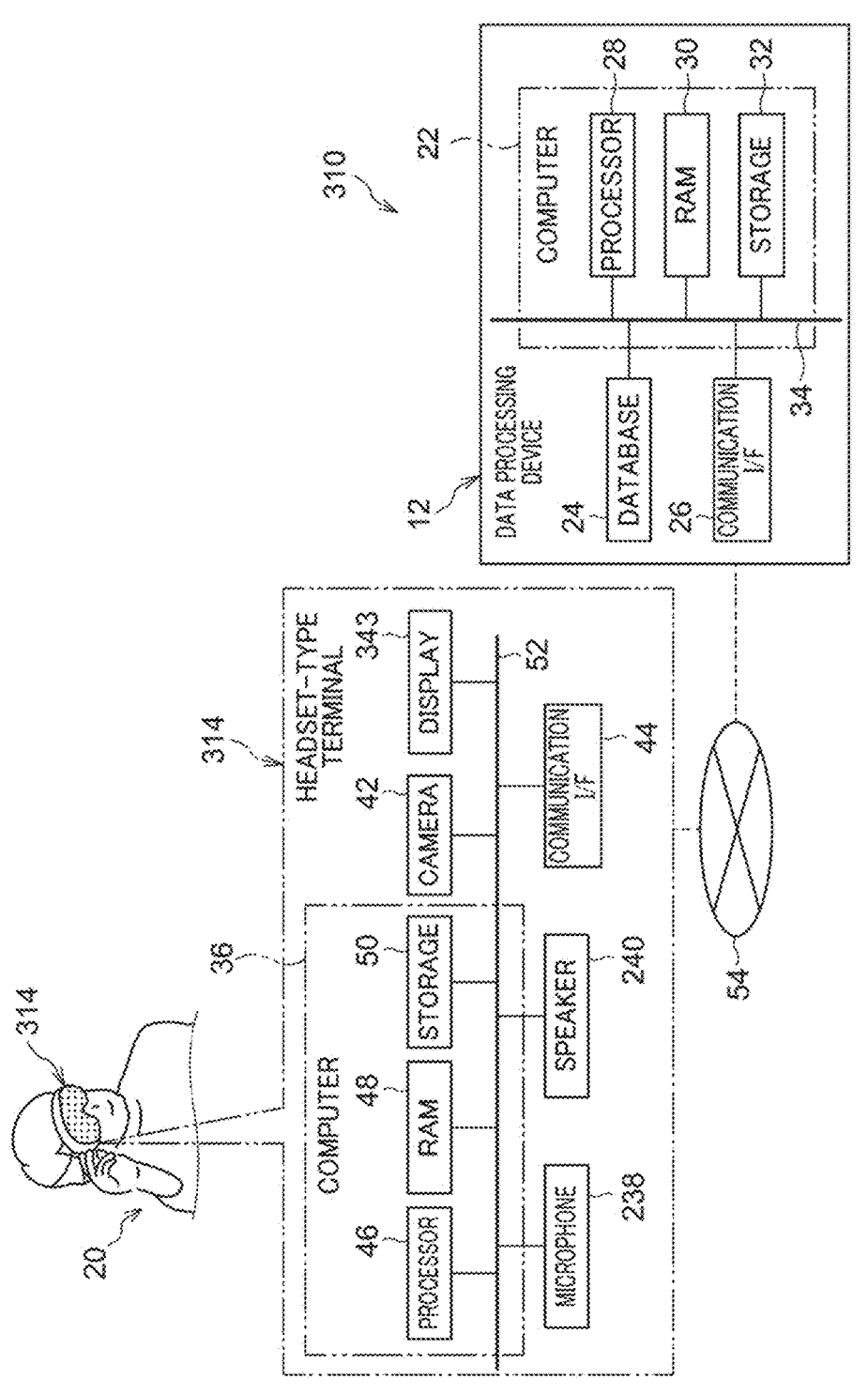
FIG. 5 is a schematic diagram illustrating an example of a configuration of a data processing system according to a third exemplary embodiment.

FIG. 5 illustrates an example of a configuration of a data processing system 310 according to a third exemplary embodiment.

As illustrated in FIG. 5, the data processing system 310 includes a data processing device 12 and a headset-type terminal 314. A server is an example of the data processing device 12.

The data processing device 12 includes a computer 22, a database 24, and a communication I/F 26. The computer 22 is an example of a "computer" according to technology disclosed herein. The computer 22 includes a processor 28, RAM 30, and storage 32. The processor 28, the RAM 30, and the storage 32 are connected to a bus 34. The database 24 and the communication I/F 26 are also connected to the bus 34. The communication I/F 26 is connected to a network 54. Examples of the network 54 include a Wide Area Network (WAN) and/or a local area network (LAN).

The headset-type terminal 314 includes a computer 36, a microphone 238, a speaker 240, a camera 42, a communication I/F 44, and a display 343. The computer 36 includes a processor 46, RAM 48, and storage 50. The processor 46, the RAM 48, and the storage 50 are connected to a bus 52. The microphone 238, the speaker 240, the camera 42, the display 343, and the communication I/F 44 are also connected to the bus 52.

The microphone 238 receives an instruction or the like from a user 20 by receiving speech uttered by the user 20. The microphone 238 captures the speech uttered by the user 20, converts the captured speech into audio data, and outputs the audio data to the processor 46. The speaker 240 outputs audio under instruction from the processor 46.

The camera 42 is a compact digital camera installed with an optical system such as a lens, an aperture, a shutter, and the like, and with an imaging device such as a complementary metal-oxide semiconductor (CMOS) image sensor or a charge coupled device (CCD) image sensor or the like. The camera 42 images the surroundings of the user 20 (for example, an imaging range defined by an angle of view equivalent to the width of visual field of an ordinary healthy subject).

The communication I/F 44 is connected to the network 54. The communication I/F 44 and the communication I/F 26 perform the role of exchanging various information between the processor 46 and the processor 28 over the network 54. The exchange of various information between the processor 46 and the processor 28 is performed in a secure state using the communication I/F 44 and the communication I/F 26.

Figure 6:
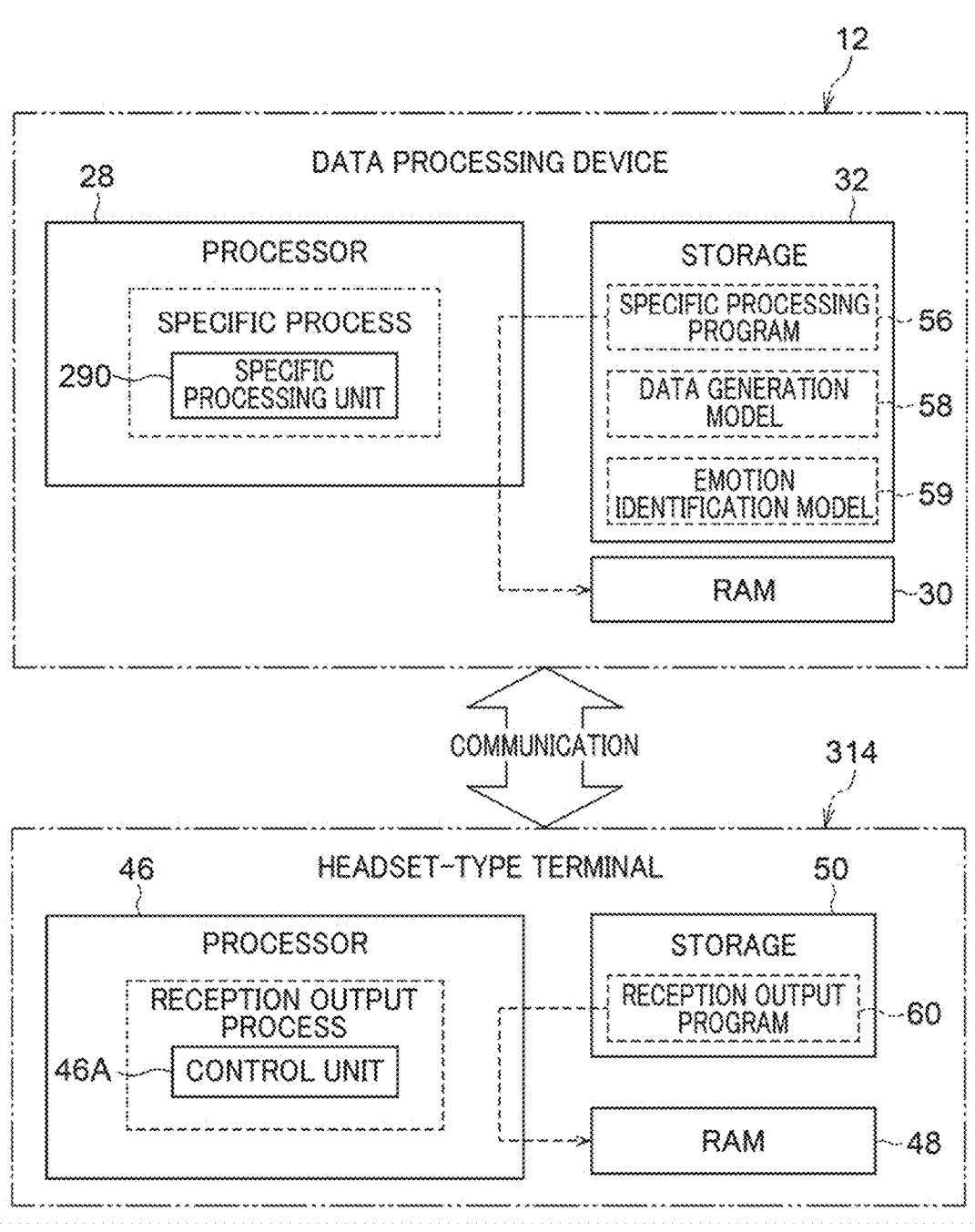
FIG. 6 is a schematic diagram illustrating an example of relevant functions of a data processing device and a headset-type terminal according to the third exemplary embodiment.

FIG. 6 illustrates an example of relevant functions of the data processing device 12 and the headset-type terminal 314. As illustrated in FIG. 6, specific processing is performed by the processor 28 in the data processing device 12. A specific processing program 56 is stored in the storage 32.

The specific processing program 56 is an example of a "program" according to technology disclosed herein. The processor 28 reads the specific processing program 56 from the storage 32, and in the RAM 30 executes the read specific processing program 56. The specific processing is implemented by the processor 28 operating as the specific processing unit 290 according to the specific processing program 56 executed in the RAM 30.

The data generation model 58 and the emotion identification model 59 are stored in the storage 32. The data generation model 58 and the emotion identification model 59 are employed by the specific processing unit 290.

Reception and output processing is performed by the processor 46 in the headset-type terminal 314. A reception and output program 60 is stored in the storage 50. The processor 46 reads the reception and output program 60 from the storage 50, and in the RAM 48 executes the read reception and output program 60. The reception and output processing is implemented by the processor 46 operating as the control unit 46A according to the reception and output program 60 executed in the RAM 48.

Next, description follows regarding the specific processing by the specific processing unit 290 of the data processing device 12. The units of the system described below are implemented by the data processing device 12 and the headset-type terminal 314. In the following description the data processing device 12 is called a "server", and the headset-type terminal 314 is called a "terminal".

Example 1

Explanation of flow will be omitted due to being similar to a flow of the specific processing in Example 1 as described in the first exemplary embodiment above.

Application Example 1

Explanation of flow will be omitted due to being similar to a flow of the specific processing in Application Example 1 as described in the first exemplary embodiment above.

Example 2

Explanation of flow will be omitted due to being similar to a flow of the specific processing in Example 2 as described in the first exemplary embodiment above.

Application Example 2

Explanation of flow will be omitted due to being similar to a flow of the specific processing in Application Example 2 as described in the first exemplary embodiment above.

The specific processing unit 290 transmits a result of the specific processing to the headset-type terminal 314. In the headset-type terminal 314, the control unit 46A outputs the result of the specific processing to the speaker 240 and the display 343. The microphone 238 acquires audio representing user input in response to the specific processing result. The control unit 46A transmits audio data representing the user input as acquired by the microphone 238 to the data processing device 12. The specific processing unit 290 in the data processing device 12 acquires the audio data.

The data generation model 58 is a so-called generative artificial intelligence (AI). Examples of the data generation model 58 include generative AIs such as ChatGPT (registered trademark) (Internet search <URL: https://openai.com/blog/chatgpt>) and the like. The data generation model 58 is obtained by performing deep learning with a neural network. The data generation model 58 is input with a prompt including an instruction, and is input with inference data such as audio data representing speech, text data representing text, image data representing images (for example, still image data or video data), and the like. The data generation model 58 takes the input inference data, performs inference according to the instruction indicated in the prompt, and outputs an inference result in one or more data format from out of audio data, text data, image data, or the like. The data generation model 58 includes, for example, a text generative AI, an image generative AI, a multimodal generative AI, or the like. Reference here to inference indicates, for example, analysis, classification, prediction, and/or abstraction etc. The specific processing unit 290 performs the specific processing referred to above while using the data generation model 58. The data generation model 58 may be a model fine-tuned so as to output an inference result from a prompt not including an instruction, and in such cases the data generation model 58 is able to output an inference result from the prompt not including an instruction. There are plural types of the data generation model 58 included in the data processing device 12 or the like, and the data generation models 58 include an AI other than a generative AI. An AI other than a generative AI is, for example, a linear regression, a logistic regression, a decision tree, a random forest, a support vector machine (SVM), a k-means clustering, a convolutional neural network (CNN), a recurrent neural network (RNN), a generative adversarial network (GAN), a naïve Bayes, or the like and is capable of performing various processing, however there is no limitation to such examples. The AI may be an AI agent. Moreover, when the processing of each of the units mentioned above is performed by an AI, this processing is partly or entirely performed by the AI, however there is no limitation to such examples. Moreover, processing executed by an AI including a generative AI may be switched to rule-based processing, and rule-based processing may be switched to processing executed by an AI including a generative AI.

Although the processing by the data processing system 10 described above is executed by the specific processing unit 290 of the data processing device 12 or by the control unit 46A of the headset-type terminal 314, the processing may be executed by a specific processing unit 290 of the data processing device 12 and a control unit 46A of the headset-type terminal 314. Moreover, the specific processing unit 290 of the data processing device 12 acquires and collects information needed for processing from the headset-type terminal 314 or from an external device or the like, and the headset-type terminal 314 acquires and collects information needed for processing from the data processing device 12 or from an external device or the like.

For example, the collection unit is implemented by the control unit 46A of the headset-type terminal 314 and/or by the specific processing unit 290 of the data processing device 12. For example, an acquisition unit acquires number-of-steps data using the camera 42 and/or the communication I/F 44 of the headset-type terminal 314, and the number-of-steps data is processed by the specific processing unit 290 of the data processing device 12.

For example, an analysis unit implemented by the specific processing unit 290 of the data processing device 12 analyzes data from the collection unit and the acquisition unit. For example, a generation unit implemented by the specific processing unit 290 of the data processing device 12 generates a cooking menu using a generative AI. For example, a supply unit implemented by the speaker 240 and the display 343 of the headset-type terminal 314 and/or the specific processing unit 290 of the data processing device 12 supplies the generated cooking menu to the user. Correspondence relationships of each unit to devices and control units are not limited to the examples described above, and various modifications thereof are possible.

The above exemplary embodiment gives an implementation example in which the specific processing is performed by the data processing device 12, however technology disclosed herein is not limited thereto, and the specific processing may be performed by the headset-type terminal 314.

Fourth Exemplary Embodiment

Figure 7:
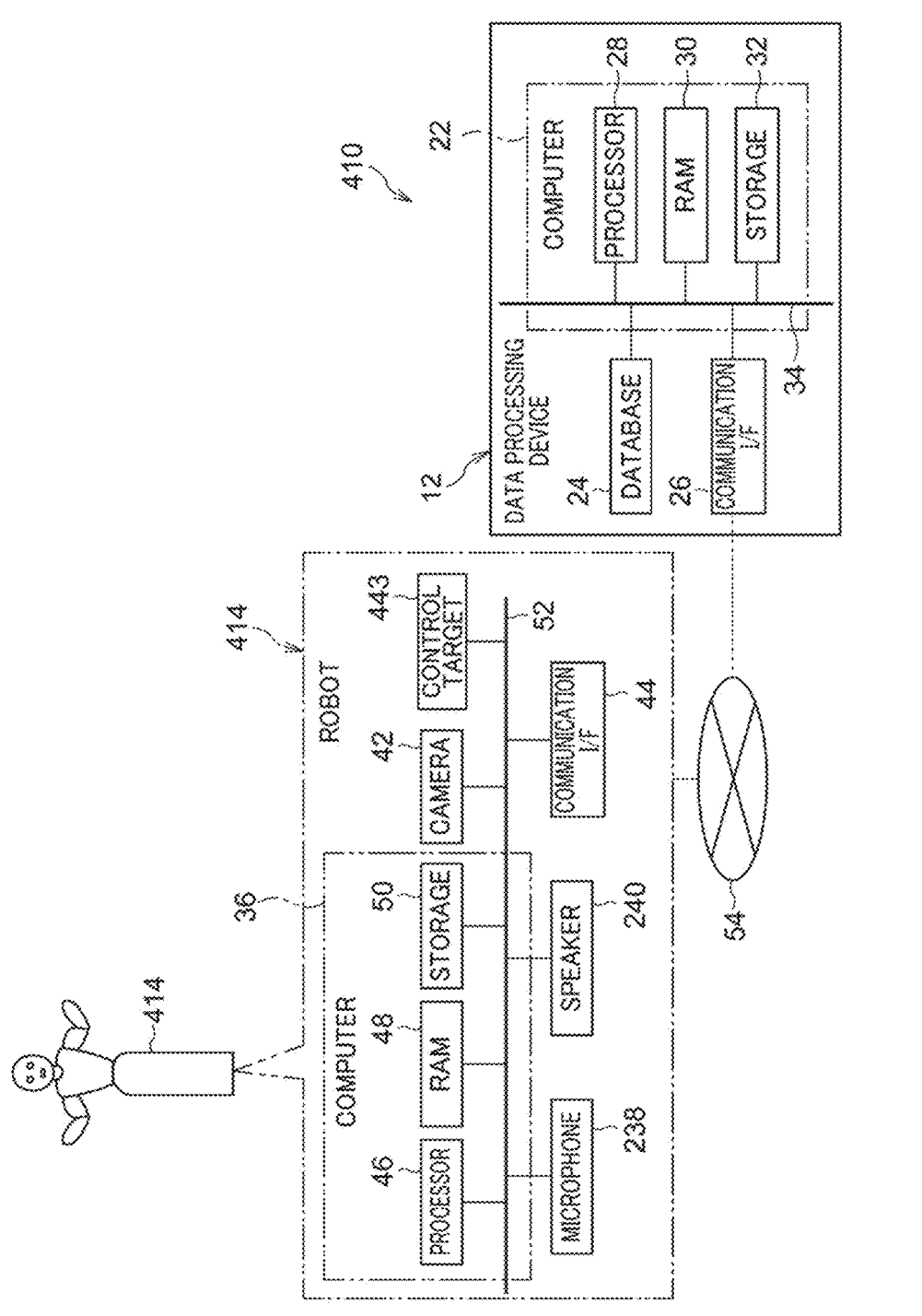
FIG. 7 is a schematic diagram illustrating an example of a configuration of a data processing system according to a fourth exemplary embodiment.

FIG. 7 illustrates an example of a configuration of a data processing system 410 according to a fourth exemplary embodiment As illustrated in FIG. 7, the data processing system 410 includes a data processing device 12 and a robot 414. A server is an example of the data processing device 12.

The data processing device 12 includes a computer 22, a database 24, and a communication I/F 26. The computer 22 is an example of a "computer" according to technology disclosed herein. The computer 22 includes a processor 28, RAM 30, and storage 32. The processor 28, the RAM 30, and the storage 32 are connected to a bus 34. The database 24 and the communication I/F 26 are also connected to the bus 34. The communication I/F 26 is connected to a network 54. Examples of the network 54 include a Wide Area Network (WAN) and/or a local area network (LAN).

The robot 414 includes a computer 36, a microphone 238, a speaker 240, a camera 42, a communication I/F 44, and a control target 443. The computer 36 includes a processor 46, RAM 48, and storage 50. The processor 46, the RAM 48, and the storage 50 are connected to a bus 52. The microphone 238, the speaker 240, the camera 42, the control target 443, and the communication I/F 44 are also connected to the bus 52.

The microphone 238 receives an instruction or the like from a user 20 by receiving speech uttered by the user 20. The microphone 238 captures the speech uttered by the user 20, converts the captured speech into audio data, and outputs the audio data to the processor 46. The speaker 240 outputs audio under instruction from the processor 46.

The camera 42 is a compact digital camera installed with an optical system such as a lens, an aperture, a shutter, and the like, and with an imaging device such as a complementary metal-oxide semiconductor (CMOS) image sensor or a charge coupled device (CCD) image sensor or the like. The camera 42 images the surroundings of the robot 414 (for example, with an imaging range defined by an angle of view equivalent to the width of visual field of an ordinary healthy subject).

The communication I/F 44 is connected to the network 54. The communication I/F 44 and the communication I/F 26 perform the role of exchanging various information between the processor 46 and the processor 28 over the network 54. The exchange of various information between the processor 46 and the processor 28 is performed in a secure state using the communication I/F 44 and the communication I/F 26.

The control target 443 includes a display device, eye LEDs, and motors to drive arms, hands, feet, and the like. The posture and gesture of the robot 414 are controlled by controlling the motors of the arms, hands, feet, and the like. Part of an emotion of the robot 414 can be expressed by controlling these motors. Moreover, a facial expression of the robot 414 can be represented by controlling an illumination state of the eye LEDs of the robot 414.

Figure 8:
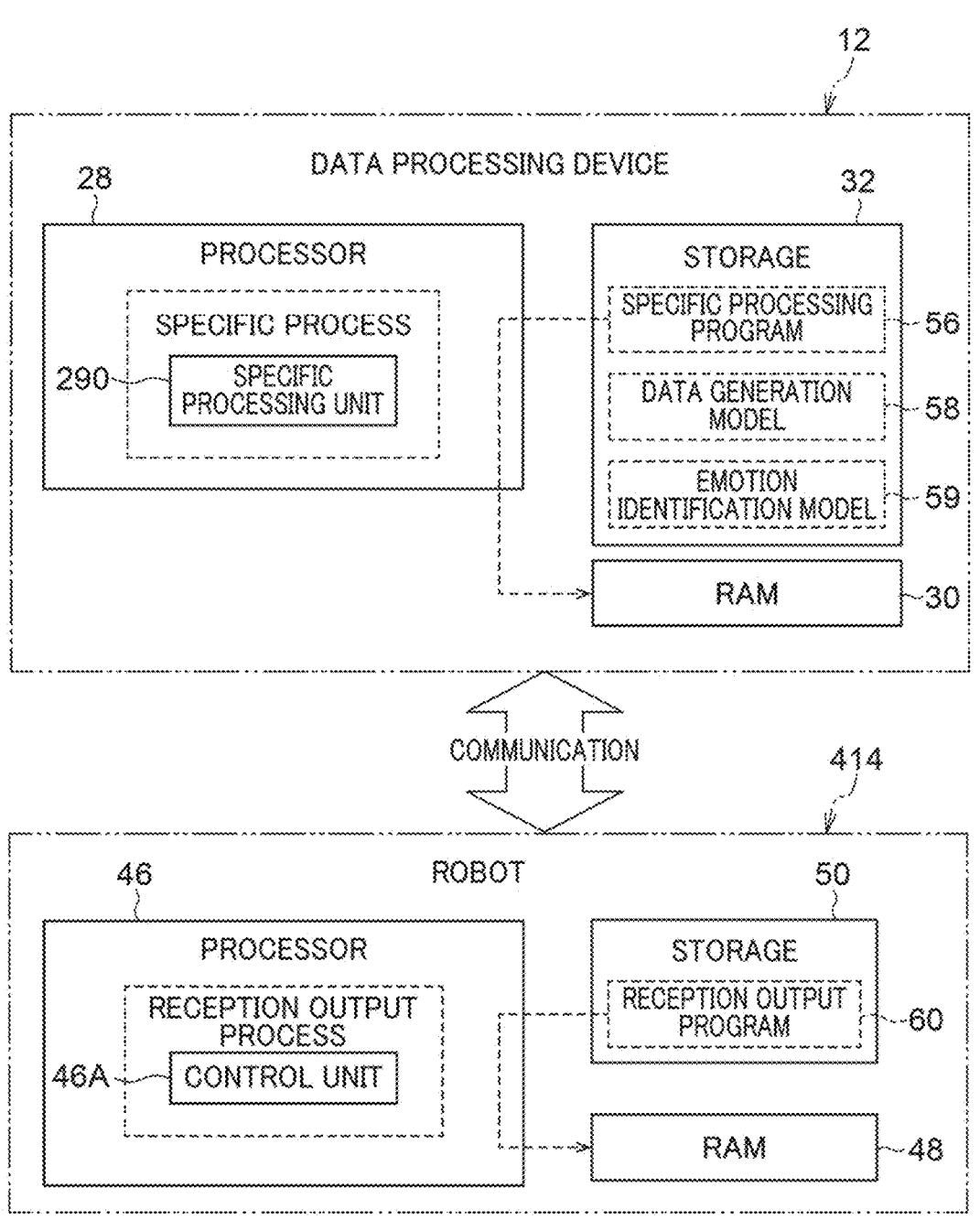
FIG. 8 is a schematic diagram illustrating an example of relevant functions of a data processing device and a robot according to the fourth exemplary embodiment.

FIG. 8 illustrates an example of relevant functions of the data processing device 12 and the robot 414. As illustrated in FIG. 8, specific processing is performed by the processor 28 in the data processing device 12. A specific processing program 56 is stored in the storage 32.

The specific processing program 56 is an example of a "program" according to technology disclosed herein. The processor 28 reads the specific processing program 56 from the storage 32, and in the RAM 30 executes the read specific processing program 56. The specific processing is implemented by the processor 28 operating as the specific processing unit 290 according to the specific processing program 56 executed in the RAM 30.

The data generation model 58 and the emotion identification model 59 are stored in the storage 32. The data generation model 58 and the emotion identification model 59 are employed by the specific processing unit 290.

Reception and output processing is performed by the processor 46 in the robot 414. A reception and output program 60 is stored in the storage 50. The processor 46 reads the reception and output program 60 from the storage 50, and in the RAM 48 executes the read reception and output program 60. The reception and output processing is implemented by the processor 46 operating as the control unit 46A according to the reception and output program 60 executed in the RAM 48.

Next, description follows regarding the specific processing by the specific processing unit 290 of the data processing device 12. The units of the system described below are implemented by the data processing device 12 and the robot 414. In the following description the data processing device 12 is called a "server", and the robot 414 is called a "terminal".

Example 1

Explanation of flow will be omitted due to being similar to a flow of the specific processing in Example 1 as described in the first exemplary embodiment above.

Application Example 1

Explanation of flow will be omitted due to being similar to a flow of the specific processing in Application Example 1 as described in the first exemplary embodiment above.

Example 2

Explanation of flow will be omitted due to being similar to a flow of the specific processing in Example 2 as described in the first exemplary embodiment above.

Application Example 2

Explanation of flow will be omitted due to being similar to a flow of the specific processing in Application Example 2 as described in the first exemplary embodiment above.

The specific processing unit 290 transmits a result of the specific processing to the robot 414. In the robot 414, the control unit 46A outputs the result of the specific processing to the speaker 240 and the control target 443. The microphone 238 acquires audio representing user input in response to the specific processing result. The control unit 46A transmits audio data representing the user input as acquired by the microphone 238 to the data processing device 12. The specific processing unit 290 in the data processing device 12 acquires the audio data.

The data generation model 58 is a so-called generative artificial intelligence (AI). Examples of the data generation model 58 include generative AIs such as ChatGPT (registered trademark) (Internet search <URL: https://openai.com/blog/chatgpt>) and the like. The data generation model 58 is obtained by performing deep learning with a neural network. The data generation model 58 is input with a prompt including an instruction, and is input with inference data such as audio data representing speech, text data representing text, image data representing images (for example, still image data or video data), and the like. The data generation model 58 takes the input inference data, performs inference according to the instruction indicated in the prompt, and outputs an inference result in one or more data format from out of audio data, text data, image data, or the like. The data generation model 58 includes, for example, a text generative AI, an image generative AI, a multimodal generative AI, or the like. Reference here to inference indicates, for example, analysis, classification, prediction, and/or abstraction etc. The specific processing unit 290 performs the specific processing referred to above while using the data generation model 58. The data generation model 58 may be a model fine-tuned so as to output an inference result from a prompt not including an instruction, and in such cases the data generation model 58 is able to output an inference result from the prompt not including an instruction. There are plural types of the data generation model 58 included in the data processing device 12 or the like, and the data generation models 58 include an AI other than a generative AI. An AI other than a generative AI is, for example, a linear regression, a logistic regression, a decision tree, a random forest, a support vector machine (SVM), a k-means clustering, a convolutional neural network (CNN), a recurrent neural network (RNN), a generative adversarial network (GAN), a naïve Bayes, or the like and is capable of performing various processing, however there is no limitation to such examples. The AI may be an AI agent. Moreover, when the processing of each of the units mentioned above is performed by an AI, this processing is partly or entirely performed by the AI, however there is no limitation to such examples. Moreover, processing executed by an AI including a generative AI may be switched to rule-based processing, and rule-based processing may be switched to processing executed by an AI including a generative AI.

Although the processing by the data processing system 10 described above is executed by the specific processing unit 290 of the data processing device 12 or by the control unit 46A of the robot 414, the processing may be executed by a specific processing unit 290 of the data processing device 12 and a control unit 46A of the robot 414. Moreover, the specific processing unit 290 of the data processing device 12 acquires and collects information needed for processing from the robot 414 or from an external device or the like, and the robot 414 acquires and collects information needed for processing from the data processing device 12 or from an external device or the like.

For example, the collection unit is implemented by the control unit 46A of the robot 414 and/or by the specific processing unit 290 of the data processing device 12. For example, an acquisition unit acquires number-of-steps data using the camera 42 and/or the communication I/F 44 of the robot 414, and the number-of-steps data is processed by the specific processing unit 290 of the data processing device 12. For example, an analysis unit implemented by the specific processing unit 290 of the data processing device 12 analyzes data from the collection unit and the acquisition unit. For example, a generation unit implemented by the specific processing unit 290 of the data processing device 12 generates a cooking menu using a generative AI. For example, a supply unit implemented by the speaker 240 and the control target 443 of the robot 414 and/or the specific processing unit 290 of the data processing device 12 supplies the generated cooking menu to the user. Correspondence relationships of each unit to devices and control units are not limited to the examples described above, and various modifications thereof are possible.

The above exemplary embodiment gives an implementation example in which the specific processing is performed by the data processing device 12, however technology disclosed herein is not limited thereto, and the specific processing may be performed by the robot 414.

Note that the emotion identification model 59 serves as an emotion engine, and may decide the emotion of a user according to a specific mapping. Specifically, the emotion identification model 59 may decide the emotion of a user according to an emotion map (see FIG. 9) that is a specific mapping. Moreover, the emotion identification model 59 may also decide the emotion of the robot similarly, and the specific processing unit 290 may be configured so as to perform the specific processing using the emotion of the robot.

Figure 9:
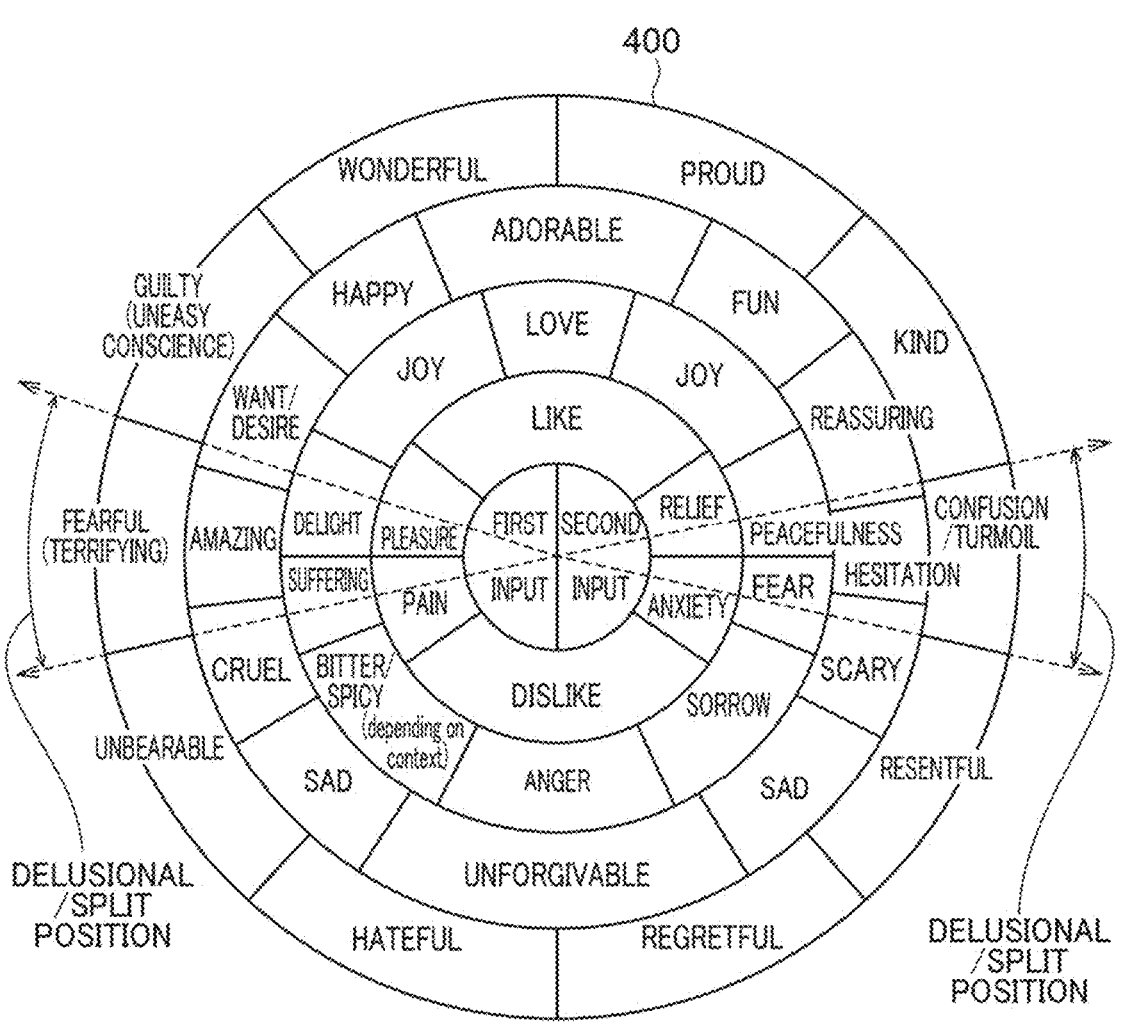
FIG. 9 illustrates an emotion map mapping plural emotions.

FIG. 9 is a diagram illustrating an emotion map 400 mapping plural emotions. In the emotion map 400, emotions are arranged in concentric circles that radiate out from the center. Primitive states of emotion are arranged nearer to the center of the concentric circles. Emotions expressing states and actions generated from states of mind are arranged further toward the outside of the concentric circles. Emotions are defined as including both affect and mental states. Emotions generated from reactions occurring in the brain are generally arranged at the left side of the concentric circles. Emotions induced by situational assessment are generally arranged at the right side of the concentric circles. Emotions generated from reactions occurring in the brain that are also emotions induced by situational assessment are generally arranged toward the top and toward the bottom of the concentric circles. Moreover, emotions of "euphoria" are arranged at the upper side of the concentric circles, and emotions of "dysphoria" are arranged at the lower side of the concentric circles. Plural emotions are accordingly mapped in this manner in the emotion map 400 based on a structure giving rise to emotions, and emotions that readily occur at the same time are mapped close to each other.

An example of such emotions is a distribution of emotions in the direction of 3 o'clock on the emotion map 400, generally around a boundary between relief and anxiety.

Situational awareness dominates over internal sensations in the right half of the emotion map 400, with an impression of calm.

The inside of the emotion map 400 represents feelings, and the outside of the emotion map 400 represents actions, and so emotions further toward the outside of the emotion map 400 are more visible (are expressed by actions).

Human emotions are based on various balances, such as posture and blood sugar value balances, with a state of dysphoria being exhibited when these balances are far from ideal and a state of euphoria being exhibited when these balances are near to ideal. Even in a robot, a car, a motorbike, or the like, emotions can be thought of as being based on various balances such as orientation and remaining battery balances, with a state called dysphoria being exhibited when these balances are far from ideal and a state called euphoria being exhibited when these balances are near to ideal. An emotion map may, for example, be generated based on the emotion map of Dr. Mitsuyoshi (PhD Dissertation https://ci.nii.ac.jp/naid/500000375379: "Research on the phonetic recognition of feelings and a system for emotional physiological brain signal analysis", Tokushima University).

Emotions belonging to an area called "reaction" where feeling dominates are arranged in the left half of the emotion map. Moreover, emotions belonging to an area called "situation" where situational awareness dominates are arranged in the right half of the emotion map.

There are two types of emotion that facilitate leaning in an emotion map. One is an emotion in the vicinity of the center of negative "penitence" and "reflection" on the situational side. In other words, sometimes a negative "emotion" such as "I don't want to feel this way ever again" and "I don't want to be chided again" is experienced in a robot. Another is a positive emotion in the area of "desire" on the reaction side. In other words, there are times when a positive feeling such as "desire more" and "want to know more" is experienced.

Figure 10:
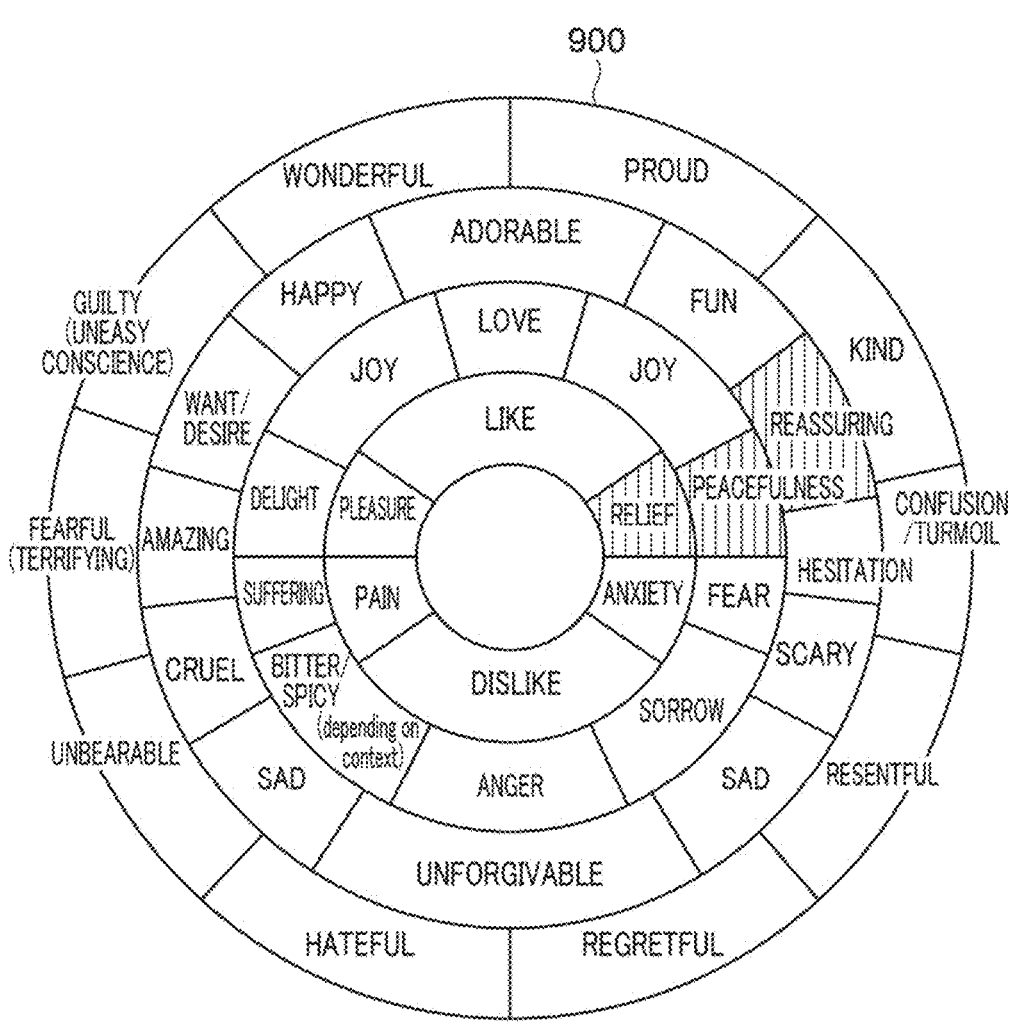
FIG. 10 illustrates an emotion map mapping plural emotions.

In the emotion identification model 59, user input is input to a pre-trained neural network, and emotion values indicating emotions shown on the emotion map 400 are acquired and the emotions of the user are decided. This neural network is pre-trained based on plural training data sets that each combine a user input with an emotion value indicating an emotion shown on the emotion map 400. The neural network is also trained such that emotions arranged close to each other have values that are close to each other, as in an emotion map 900 illustrated in FIG. 10. In FIG. 10 the plural emotions of "relief", "peaceful", and "reassured" are indicated as an example of close emotion values.

Although the system according to the present disclosure has been described mainly as functions of the data processing device 12, the system according to the present disclosure is not limited to being implemented in a server. The system according to the present disclosure may be implemented as a general information processing system. The present disclosure may, for example, be implemented by a software program operating on a personal computer, and may be implemented by an application operating on a smartphone or the like. The method according to the present disclosure may also be supplied to a user in the form of Software as a Service (SaaS).

Although in the exemplary embodiments described above examples are given of embodiments in which the specific processing is performed by a single computer 22, technology disclosed herein is not limited thereto, and distributed processing may be performed for the specific processing, with the specific processing distributed across plural computers including the computer 22. For example, the data generation model 58 may be provided in a device external to the data processing device 12, such that data generation in response to input data is performed in the external device.

Although in the exemplary embodiments described above examples are described of embodiments in which the specific processing program 56 is stored in the storage 32, the technology disclosed herein is not limited thereto. For example, the specific processing program 56 may be stored on a portable, non-transitory, computer readable, storage medium, such as universal serial bus (USB) memory or the like. The specific processing program 56 stored on the non-transitory storage medium is then installed on the computer 22 of the data processing device 12. The processor 28 then executes the specific processing according to the specific processing program 56.

Moreover, the specific processing program 56 may be stored on a storage device, such as a server connected to the data processing device 12 over the network 54, with the specific processing program 56 then being downloaded in response to a request from the data processing device 12 and installed on the computer 22.

Note that there is no need to store the entire specific processing program 56 on the storage device, such as a server connected to the data processing device 12 over the network 54, or to store the entire specific processing program 56 on the storage 32, and part of the specific processing program 56 may be stored thereon.

Hardware resources for executing the specific processing may use various processors as listed below. Examples of processors include, for example, a CPU that is a general-purpose processor that functions as a hardware resource to execute the specific processing by executing software, namely a program. Moreover, the processor may, for example, be a dedicated electronic circuit that is a processor having a circuit configuration custom designed for executing the specific processing, such as a field-programmable gate array (FPGA), a programmable logic device (PLD), or an application specific integrated circuit (ASIC).

Memory is inbuilt or connected to each of these processors, and the specific processing is executed by each of these processors using the memory.

The hardware resource that executes the specific processing may be configured from one of these various processors, or may be configured from a combination of two or more processors of the same or different type (for example, a combination of plural FPGAs, or a combination of a CPU and a FPGA). The hardware resource executing the specific processing may be a single processor.

Examples of configurations of a single processor include, firstly, a configuration of a single processor resulting from combining one or more CPU and software, in an embodiment in which this processor functions as the hardware resource for executing the specific processing. Secondly, as typified by a System-on-chip (SOC) or the like, there is also an embodiment that uses a processor realized by a single IC chip to function as an overall system including plural hardware resources for executing the specific processing. Adopting such an approach means that the specific processing is realized using one or more of the various processors described above as hardware resource.

Furthermore, more specifically, an electrical circuit that combines circuit elements such as semiconductor elements or the like may be employed as a hardware structure of these various processors. The specific processing is merely an example thereof. This means that obviously redundant steps may be omitted, new steps may be added, and the processing sequence may be swapped around within a range not departing from the spirit of the present disclosure.

The described content and drawing content illustrated above are a detailed description of parts according to the present disclosure, and are merely examples of the present disclosure. For example, description related to the above configuration, function, operation, and advantageous effects is a description related to examples of the configuration, function, operation, and advantageous effects of parts according to the present disclosure.

This means that obviously redundant parts may be eliminated, new elements may be added, and switching around may be performed on the described content and drawing content illustrated above within a range not departing from the spirit of the present disclosure.

Moreover, to avoid misunderstanding and to facilitate understanding of parts according to the present disclosure, description related to common knowledge in the art and the like not particularly needing description to enable implementation of the present disclosure is omitted in the described content and drawing content illustrated as described above.

All publications, patent applications and technical standards mentioned in the present specification are incorporated by reference in the present specification to the same extent as if each individual publication, patent application, or technical standard was specifically and individually indicated to be incorporated by reference.

Note that, regarding the above description, the following supplementary notes are further disclosed.

Example 1

(Supplementary 1)

A system comprising a processor, wherein the processor is configured to:

acquire biosignal data by means of a wearable garment arranged to maintain close contact with a user's body, said garment comprising at least a biosignal detection device and a stimulation signal generation device, control a control device connected to the garment for managing the biosignal detection device and the stimulation signal generation device, establish wireless communication between the control device and an information processing device, analyze the acquired biosignal data and calculate a user state index using a generative artificial intelligence model implemented on the information processing device, generate, by the generative artificial intelligence model and based on a prompt sentence, an individualized stimulation signal pattern according to the biosignal data and usage context, transmit the stimulation signal pattern from the information processing device to the control device, and control the stimulation signal generation device in accordance with the received stimulation signal pattern.

(Supplementary 2)

The system according to supplementary 1, wherein the processor is configured to operate the control device using an integrated power storage element as a power source.

(Supplementary 3)

The system according to supplementary 1, wherein the processor is configured to learn from evaluation data received from the user and, based on results of such learning, optimize subsequent individualized operation instructions generated by the generative artificial intelligence model.

Application Example 1

(Supplementary 1)

A system comprising a processor, wherein the processor is configured to:

acquire biometric information from a user wearing a biometric data acquiring garment equipped with a plurality of detection elements arranged to contact the user's body surface, control a plurality of low-frequency stimulation elements embedded in the biometric data acquiring garment via a control unit, wirelessly communicate with an external computing device configured to collect the acquired biometric information from the detection elements, transmit the biometric information from the computing device to a server, cause the server to analyze at least the biometric information and estimated emotional state of the user using a generative artificial intelligence model to generate a control command including a massage pattern, receive the control command at the computing device and cause, through the control unit, the plurality of low-frequency stimulation elements to be controlled automatically according to the control command, acquire experience evaluation information from the user through the computing device, transmit the experience evaluation information to the server, and update a learning dataset of the generative artificial intelligence model based on the experience evaluation information to optimize subsequent control command generation, and display the control command content or massage information to the user via a presentation device.

(Supplementary 2)

The system according to supplementary 1, wherein the processor is configured to supply power to the control unit using a power storage member embedded in the control unit.

(Supplementary 3)

The system according to supplementary 1, wherein the processor is configured to update the generative artificial intelligence model based on the experience evaluation information acquired from the user in order to improve subsequent control command generation.

Example 2

(Supplementary 1)

A system comprising a processor, wherein the processor is configured to:

acquire biometric data and emotional data from a covering article that is in close contact with a biological information acquisition target, the covering article including a biometric information acquisition unit and an electrical stimulation output unit;

analyze a biological state and an emotional state of a user based on the acquired biometric data and emotional data;

generate control instruction information for the electrical stimulation output unit according to the state of the user, using a generative information processing algorithm and based on analysis results;

transmit the control instruction information to a control device that wirelessly communicates with the processor and controls the output position, output intensity, and output rhythm of the electrical stimulation output unit;

receive evaluation information provided by the user after an electrical stimulation session, and update the control instruction information for a subsequent session based on the evaluation information; and execute at least the analysis and generation using a server device on a cloud network.

(Supplementary 2)

The system according to supplementary 1, wherein the processor is configured to supply power to the control device using a power supply unit housed within the control device.

(Supplementary 3)

The system according to supplementary 1, wherein the processor is configured to use a predefined instruction generation sentence as a prompt for the generative information processing algorithm and generate the control instruction information according to the user's acquired biometric data and emotional data.

Application Example 2

(Supplementary 1)

A system comprising a processor, wherein the processor is configured to:

obtain biological information from an individual using a biological information acquisition medium, control a control unit arranged within the biological information acquisition medium and a physical stimulation medium, communicate with an information processing device via wireless communication, collect time-series biological information multiple times from the biological information acquisition medium, perform preprocessing, feature extraction, emotional state analysis, and relaxation index calculation using artificial intelligence processing, automatically generate a treatment program using a generative artificial intelligence model based on the processed biological information, and generate control signals for said treatment program, control, for each individual, the position, intensity, and rhythm of the physical stimulation medium according to the control signals of the treatment program, analyze feedback information received from the individual after treatment in combination with the corresponding biological information and continuously optimize the generation of the treatment program by machine learning, and generate explanation information or prompt sentences explaining the generation logic of the treatment program.

(Supplementary 2)

The system according to supplementary 1, wherein the processor is configured to supply operating power to the control unit using an electrical storage medium.

(Supplementary 3)

The system according to supplementary 1, wherein the processor is configured to adaptively change parameters of the treatment program generation algorithm of the generative artificial intelligence model by using time-series data of multiple instances of feedback information and biological information from the individual.

What is claimed is:

1. A system comprising:

a full-body fitting garment configured to be worn by a user;

low-frequency pads that are disposed within the garment, and that are configured to apply low-frequency electrical stimulation to a body of the user to provide a massage;

a display; and a processor comprising a control unit connected to the garment, wherein the processor is configured to:

collect biometric data via sensors arranged inside the garment;

analyze and calculate a user relaxation score based on the biometric data;

wirelessly connect to an external information processing device;

control the display so as to provide visualization of a relaxation state of the user based on the biometric data acquired by the sensors and relaxation score by means of an artificial intelligence module included in the information processing device;

generate operation instructions for optimizing the relaxation state of the user based on the visualized relaxation state;

generate individualized stimulation signal patterns by means of prompt sentences and usage context supplied to the artificial intelligence module; and control the low-frequency pads according to the operation instructions to deliver the individualized stimulation patterns to the user's muscles to provide a massage to the user's body.

2. The system according to claim 1, wherein the processor is further configured to supply power to the control unit using a battery incorporated within the control unit.

3. The system according to claim 1, wherein the processor is further configured to cause the artificial intelligence module to learn from user feedback and improve the operation instructions for subsequent sessions.

4. The system according to claim 1, wherein the processor is further configured to prompt the user to supply feedback about the application of the low-frequency electrical stimulation to the body of the user to provide a massage.

5. The system according to claim 1, wherein the sensors comprise a heart rate sensor, a temperature sensor and a skin conductance sensor.

6. The system according to claim 1, wherein the processor is further configured to receive emotion estimation information from the sensors, and optionally a facial recognition scan or voice tone analysis, and determine the user's emotional state, and wherein the processor is further configured to generate operation instructions for optimizing the relaxation state of the user based on the visualized relaxation state and the emotional state of the user.

\* \* \* \* \*